US007199142B2

(12) United States Patent
Chen et al.

(10) Patent No.: US 7,199,142 B2
(45) Date of Patent: Apr. 3, 2007

(54) 1-((5-ARYL-1,2,4-OXADIAZOL-3-YL) BENZYL)AZETIDINE-3-CARBOXYLATES AND 1-((5-ARYL-1,2,4-OXADIAZOL-3-YL)BENZYL) PYRROLIDINE-3-CARBOXYLATES AS EDG RECEPTOR AGONISTS

(75) Inventors: Weirong Chen, Waltham, MA (US); Jeffrey J. Hale, Westfield, NJ (US); Zhen Li, Scotch Plains, NJ (US); Christopher L. Lynch, Trevor, WI (US); Sander G. Mills, Scotch Plains, NJ (US); William E. Neway, III, Newtown, PA (US)

(73) Assignee: Merck & Co., Inc., Rahway, NJ (US)

( * ) Notice: Subject to any disclaimer, the term of this patent is extended or adjusted under 35 U.S.C. 154(b) by 98 days.

(21) Appl. No.: 10/515,192

(22) PCT Filed: Jun. 16, 2003

(86) PCT No.: PCT/US03/18852

§ 371 (c)(1),
(2), (4) Date: Nov. 19, 2004

(87) PCT Pub. No.: WO03/105771

PCT Pub. Date: Dec. 24, 2003

(65) Prior Publication Data

US 2005/0245575 A1 Nov. 3, 2005

Related U.S. Application Data

(60) Provisional application No. 60/389,173, filed on Jun. 17, 2002.

(51) Int. Cl.
*C07D 271/06* (2006.01)
*A61K 31/4245* (2006.01)

(52) U.S. Cl. ..................................... 514/364; 548/131

(58) Field of Classification Search ..................... None
See application file for complete search history.

(56) References Cited

U.S. PATENT DOCUMENTS

| | | | | |
|---|---|---|---|---|
| 4,096,273 | A | 6/1978 | Gutman | |
| 6,200,978 | B1 * | 3/2001 | Maw et al. | 514/254.05 |
| 6,277,873 | B1 | 8/2001 | Yu et al. | |

FOREIGN PATENT DOCUMENTS

| | | | |
|---|---|---|---|
| EP | 0454444 | A1 | 4/1991 |
| EP | 1070708 | B1 | 7/2000 |
| WO | WO 97/44333 | | 11/1997 |
| WO | WO98/31681 | | 7/1998 |
| WO | WO 00/00477 | | 1/2000 |
| WO | WO02/06269 | A1 | 1/2002 |

OTHER PUBLICATIONS

Rice et al., "An Improved Synthesis of 1,2,4-Oxadizaoles on Solid Support," Bioorganic Medicinal Chemistry Letters, vol. 11, pp. 753-755 (2001).*

* cited by examiner

*Primary Examiner*—Kamal A. Saeed
*Assistant Examiner*—Andrew B. Freistein
(74) *Attorney, Agent, or Firm*—Raynard Yuro; David L. Rose

(57) ABSTRACT

The present invention encompasses compounds of Formula I: as well as the pharmaceutically acceptable salts and hydrates thereof. The compounds are useful for treating immune mediated diseases and conditions, such as bone marrow, organ and tissue transplant rejection. Pharmaceutical compositions and methods of use are included.

12 Claims, No Drawings

1-((5-ARYL-1,2,4-OXADIAZOL-3-YL)BENZYL)AZETIDINE-3-CARBOXYLATES AND 1-((5-ARYL-1,2,4-OXADIAZOL-3-YL)BENZYL)PYRROLIDINE-3-CARBOXYLATES AS EDG RECEPTOR AGONISTS

CROSS REFERENCE TO RELATED APPLICATIONS

This application is a U.S. National Phase application under 35 U.S.C. § 371 of PCT Application No. PCT/US03/18852, filed Jun. 16, 2003, which claims priority under 35 U.S.C. 119 to U.S. No. 60/389,173, filed Jun. 17, 2002.

BACKGROUND OF THE INVENTION

The present invention is related to compounds that are $S1P_1$/Edg1 receptor agonists and thus have immunosuppressive activities by producing lymphocyte sequestration in secondary lymphoid tissues. The invention is also directed to pharmaceutical compositions containing such compounds and methods of treatment or prevention.

Immunosuppressive agents have been shown to be useful in a wide variety of autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves ophthalmopathy, atopic dermatitis and asthma. They have also proved useful as part of chemotherapeutic regimens for the treatment of cancers, lymphomas and leukemias.

Although the underlying pathogenesis of each of these conditions may be quite different, they have in common the appearance of a variety of autoantibodies and/or self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce both cellular and humoral responses including antibodies, cytokines and cytotoxic lymphocytes which lead to graft rejection.

One end result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb to infection as they are to their autoimmune disease.

Cyclosporin A is a drug used to prevent rejection of transplanted organs. FK-506 is another drug approved for the prevention of transplant organ rejection, and in particular, liver transplantation. Cyclosporin A and FK-506 act by inhibiting the body's immune system from mobilizing its vast arsenal of natural protecting agents to reject the transplant's foreign protein. Cyclosporin A was approved for the treatment of severe psoriasis and has been approved by European regulatory agencies for the treatment of atopic dermatitis.

Though they are effective in delaying or suppressing transplant rejection, Cyclosporin A and FK-506 are known to cause several undesirable side effects including nephrotoxicity, neurotoxicity, and gastrointestinal discomfort. Therefore, an immunosuppressant without these side effects still remains to be developed and would be highly desirable.

The immunosuppressive compound FTY720 is a lymphocyte sequestration agent currently in clinical trials. FTY720 is metabolized in mammals to a compound that is a potent agonist of sphingosine 1-phosphate receptors. Agonism of sphingosine 1-phosphate receptors induces the sequestration of lymphocytes (T-cells and B-cells) in lymph nodes and Peyer's patches without lymphodepletion. Such immunosuppression is desirable to prevent rejection after organ transplantation and in the treatment of autoimmune disorders.

Sphingosine 1-phosphate is a bioactive sphingolipid metabolite that is secreted by hematopoietic cells and stored and released from activated platelets. Yatomi, Y., T. Ohmori, G. Rile, P. Kazama, H. Okamoto, T. Sano, K. Satoh, S. Kume, G. Tigyi, Y. Igarashi, and Y. Ozaki. 2000. *Blood.* 96:3431–8. It acts as an agonist on a family of G protein-coupled receptors to regulate cell proliferation, differentiation, survival, and motility. Fukushima, N., I. Ishii, J. J. A. Contos, J. A. Weiner, and J. Chun. 2001. Lysophospholipid receptors. Annu. Rev. Pharmacol. Toxicol. 41:507–34; Hla, T., M.-J. Lee, N. Ancellin, J. H. Paik, and M. J. Kluk. 2001. Lysophospholipids—Receptor revelations. *Science.* 294:1875–1878; Spiegel, S., and S. Milstien. 2000. Functions of a new family of sphingosine-1-phosphate receptors. *Biochim. Biophys. Acta.* 1484:107–16; Pyne, S., and N. Pyne. 2000. Sphingosine 1-phosphate signalling via the endothelial differentiation gene family of G-protein coupled receptors. *Pharm. & Therapeutics.* 88:115–131. Five sphingosine 1-phosphate receptors have been identified ($S1P_1$, $S1P_2$, $S1P_3$, $S1P_4$, and $S1P_5$, also known as endothelial differentiation genes Edg1, Edg5, Edg3, Edg6, Edg8), that have widespread cellular and tissue distribution and are well conserved in human and rodent species (see Table). Binding to S1P receptors elicits signal transduction through Gq-, Gi/o, G12-, G13-, and Rho-dependent pathways. Ligand-induced activation of $S1P_1$ and $S1P_3$ has been shown to promote angiogenesis, chemotaxis, and adherens junction assembly through Rac- and Rho-, see Lee, M.-J., S. Thangada, K. P. Claffey, N. Ancellin, C. H. Liu, M. Kluk, M. Volpi, R. I. Sha'afi, and T. Hla. 1999. *Cell.* 99:301–12, whereas agonism of $S1P_2$ promotes neurite retraction, see Van Brocklyn, J. R., Z. Tu, L. C. Edsall, R. R. Schmidt, and S. Spiegel. 1999. *J. Biol. Chem.* 274:4626–4632, and inhibits chemotaxis by blocking Rac activation, see Okamoto, H., N. Takuwa, T. Yokomizo, N. Sugimoto, S. Sakurada, H. Shigematsu, and Y. Takuwa. 2000. *Mol. Cell. Biol.* 20:9247–9261. $S1P_4$ is localized to hematopoietic cells and tissues, see Graeler, M. H., G. Bernhardt, and M. Lipp. 1999. *Curr. Top. Microbiol. Immunol.* 246:131–6, whereas $S1P_5$ is primarily a neuronal receptor with some expression in lymphoid tissue, see Im, D. S., C. E. Heise, N. Ancellin, B. F. O'Dowd, G. J. Shei, R. P. Heavens, M. R. Rigby, T. Hla, S. Mandala, G. McAllister, S. R. George, and K. R. Lynch. 2000. *J. Biol. Chem.* 275:14281–6.

Administration of sphingosine 1-phosphate to animals induces systemic sequestration of peripheral blood lymphocytes into secondary lymphoid organs, thus resulting in therapeutically useful immunosuppression, see Mandala, S., R. Hajdu, J. Bergstrom, E. Quackenbush, J. Xie, J. Milligan, R. Thornton, G.-J. Shei, D. Card, C. Keohane, M. Rosenbach, J. Hale, C. L. Lynch, K. Rupprecht, W. Parsons, H.

Rosen. 2002. *Science.* 296:346–349. However, sphingosine 1-phosphate also has cardiovascular and bronchoconstrictor effects that limit its utility as a therapeutic agent. Intravenous administration of sphingosine 1-phosphate decreases the heart rate, ventricular contraction and blood pressure in rats, see Sugiyama, A., N. N. Aye, Y. Yatomi, Y. Ozaki, and K. Hashimoto. 2000. *Jpn. J. Pharmacol.* 82:338–342. In human airway smooth muscle cells, sphingosine 1-phosphate modulates contraction, cell growth and cytokine production that promote bronchoconstriction, airway inflammation and remodeling in asthma, see Ammit, A. J., A. T. Hastie, L. C. Edsall, R. K. Hoffman, Y. Amrani, V. P. Krymskaya, S. A. Kane, S. P. Peters, R. B. Penn, S. Spiegel, R. A. Panettieri. Jr. 2001, *FASEB J.* 15:1212–1214. The undesirable effects of sphingosine 1-phosphate are associated with its non-selective, potent agonist activity on all S1P receptors.

The present invention encompasses compounds which are agonists of the $S1P_1$/Edg1 receptor having selectivity over the $S1P_3$/Edg3 receptor. An $S1P_1$/Edg1 receptor selective agonist has advantages over current therapies and extends the therapeutic window of lymphocytes sequestration agents, allowing better tolerability with higher dosing and thus improving efficacy as monotherapy.

While the main use for immunosuppressants is in treating bone marrow, organ and transplant rejection, other uses for such compounds include the treatment of arthritis, in particular, rheumatoid arthritis, insulin and non-insulin dependent diabetes, multiple sclerosis, psoriasis, inflammatory bowel disease, Crohn's disease, lupus erythematosis and the like.

Thus, the present invention is focused on providing immunosuppressant compounds that are safer and more effective than prior compounds. These and other objects will be apparent to those of ordinary skill in the art from the description contained herein.

Summary of S1P receptors

| Name | Synonyms | Coupled G proteins | mRNA expression |
|---|---|---|---|
| $S1P_1$ | Edg1, $LP_{B1}$ | $G_{i/o}$ | Widely distributed, endothelial cells |
| $S1P_2$ | Edg5, $LP_{B2}$, AGR16, H218 | $G_{i/o}$, $G_q$, $G_{12/13}$ | Widely distributed, vascular smooth muscle cells |
| $S1P_3$ | Edg3, $LP_{B3}$ | $G_{i/o}$, $G_q$, $G_{12/13}$ | Widely distributed, endothelial cells |
| $S1P_4$ | Edg6, $LP_{C1}$ | $G_{i/o}$ | Lymphoid tissues, lymphocytic cell lines |
| $S1P_5$ | Edg8, $LP_{B4}$, NRG1 | $G_{i/o}$ | Brain, spleen |

SUMMARY OF THE INVENTION

The present invention encompasses compounds of Formula I:

I

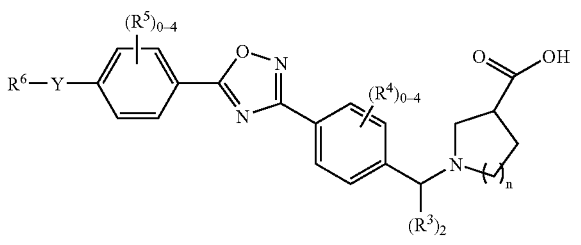

as well as the pharmaceutically acceptable salts and hydrates thereof. The compounds are useful for treating immune mediated diseases and conditions, such as bone marrow, organ and tissue transplant rejection. Pharmaceutical compositions and methods of use are included.

DETAILED DESCRIPTION OF THE INVENTION

The invention encompasses compounds represented by Formula I

I

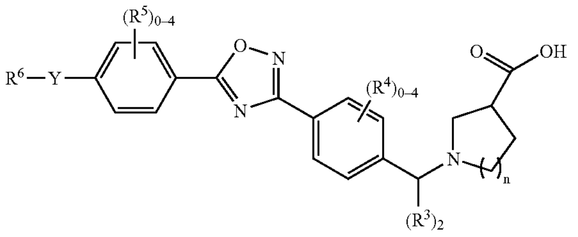

or a pharmaceutically acceptable salt or hydrate thereof, wherein:

n is 0 or 1;

Y is a bond, —O— or —$S(O)_k$—, wherein k is 0, 1 or 2;

each $R^3$ is independently selected from the group consisting of: hydrogen and $C_{1-4}$alkyl, said $C_{1-4}$alkyl optionally substituted with from one up to the maximum number of substitutable positions with a substituent independently selected from the group consisting of: halo, hydroxy, $C_{1-4}$alkoxy and carboxy;

each $R^4$ is independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo;

each $R^5$ is independently selected from the group consisting of:

(a) halo,
(b) cyano,
(c) hydroxy,
(d) —$N(R^7)_2$
(e) $C_{1-6}$alkyl,
(f) $C_{2-6}$alkenyl,
(g) $C_{3-6}$alkynyl
(h) $C_{1-6}$alkoxy
(i) $C_{1-6}$alkyl-$S(O)_k$—, wherein k is 0, 1 or 2,
(j) $C_{3-6}$cycloalkyl,
(k) phenyl, and
(l) $HET^1$;

wherein items (e) to (j) above are each optionally substituted from one up to the maximum number of substituable positions with a substituent independently selected from the group consisting of: halo, hydroxy and $C_{1-3}$alkoxy, said $C_{1-3}$alkoxy group optionally substituted from one up to the maximum number of substitutable positions with halo, and wherein items (k) and (l) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo;

$R^6$ is selected from the group consisting of:
(1) hydrogen
(2) halo,
(3) cyano,
(4) $C_{1-10}$alkyl,
(5) $C_{2-10}$alkenyl,
(6) $C_{3-10}$alkynyl,
(7) $C_{3-6}$cycloalkyl
(8) phenyl, and
(9) $HET^2$;

wherein items (4) to (6) above are each optionally substituted from one up to the maximum number of substituable positions with a substituent independently selected from the group consisting of: halo, hydroxy, $C_{3-6}$cycloalkyl, phenyl, $HET^3$ and $C_{1-3}$alkoxy, said $C_{3-6}$cycloalkyl, phenyl, $HET^3$ and $C_{1-3}$alkoxy groups optionally substituted from one up to the maximum number of substitutable positions with halo, wherein item (7) above is optionally substituted from one up to the maximum number of substituable positions with a substituent independently selected from the group consisting of: halo, hydroxy, phenyl, $HET^4$ and $C_{1-3}$alkoxy, said phenyl, $HET^4$ and $C_{1-3}$alkoxy groups optionally substituted from one up to the maximum number of substitutable positions with halo, and wherein items (8) and (9) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo, with the provsio that $R^6$ is not halo or cyano when Y is —O— or —$S(O)_k$—; or $R^6$ and one $R^5$ group or two $R^5$ groups may be joined together to form a five or six-membered monocyclic ring optionally containing 1 or 2 heteroatoms selected from the group consisting of: O, S, or $N(R^7)$, each $R^7$ is independently hydrogen or $C_{1-4}$alkyl, said $C_{1-4}$alkyl optionally substituted substituted from one up to the maximum number of substitutable positions with halo; and $HET^1$, $HET^2$, $HET^3$ and $HET^4$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

An embodiment of the invention encompasses a compound of Formula I wherein n is 0.

Another embodiment of the invention encompasses a compound of Formula I wherein n is 1.

Another embodiment of the invention encompasses a compound of Formula I wherein $R^3$ is hydrogen or methyl.

Another embodiment of the invention encompasses a compound of Formula I wherein one $R^4$ is present and said $R^4$ is halo or methyl.

Another embodiment of the invention encompasses a compound of Formula I wherein no $R^5$ is present.

Another embodiment of the invention encompasses a compound of Formula I wherein $R^6$ is selected from the group consisting of:
(1) $C_{1-10}$alkyl,
(2) $C_{2-10}$alkenyl,
(3) $C_{3-10}$alkynyl,
(4) $C_{3-6}$cycloalkyl
(5) phenyl, and
(6) $HET^2$;

wherein items (1) to (3) above are each optionally substituted from one up to the maximum number of substituable positions with a substituent independently selected from the group consisting of: halo, hydroxy, $C_{3-6}$cycloalkyl, phenyl, $HET^3$ and $C_{1-3}$alkoxy, said $C_{3-6}$cycloalkyl, phenyl, $HET^3$ and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl, $HET^4$ and $C_{1-3}$alkoxy, said phenyl, $HET^4$ and $C_{1-3}$alkoxy groups optionally substituted from one up to the maximum number of substitutable positions with halo, and wherein items (5) and (6) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo.

Within this embodiment of the invention is encompassed a compound of Formula I wherein $R^6$ is selected from the group consisting of:
(1) $C_{1-10}$alkyl,
(2) $C_{2-10}$alkenyl,
(3) $C_{3-10}$alkynyl,
(4) $C_{3-6}$cycloalkyl and
(5) phenyl, wherein items (1) to (3) above are each optionally substituted from one up to the maximum number of substituable positions with a substituent independently selected from the group consisting of: halo, hydroxy, $C_{3-6}$cycloalkyl, phenyl and $C_{1-3}$alkoxy, said $C_{3-6}$cycloalkyl, phenyl and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl and $C_{1-3}$alkoxy, said phenyl and $C_{1-3}$alkoxy groups optionally substituted from one up to the maximum number of substitutable positions with halo, and wherein item (5) above is optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo.

In another embodiment, the invention encompasses a compound of Formula Ia:

Ia

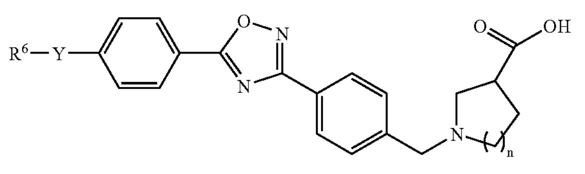

or a pharmaceutically acceptable salt or hydrate thereof, wherein:

n is 0 or 1;

Y is a bond or —O—;

$R^6$ is selected from the group consisting of:

(1) $C_{1-10}$alkyl, (2) $C_{2-10}$alkenyl, (3) $C_{3-10}$alkynyl, (4) $C_{3-6}$cycloalkyl (5) phenyl, and (6) $HET^2$;

wherein items (1) to (3) above are each optionally substituted from one up to the maximum number of substituable positions with a substituent independently selected from the group consisting of: halo, hydroxy, $C_{3-6}$cycloalkyl, phenyl, $HET^3$ and $C_{1-3}$alkoxy, said $C_{3-6}$cycloalkyl, phenyl, $HET^3$ and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl, $HET^4$ and $C_{1-3}$alkoxy, said phenyl, $HET^4$ and $C_{1-3}$alkoxy groups optionally substituted from one up to the maximum number of substitutable positions with halo, and wherein items (5) and (6) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo; and $HET^2$, $HET^3$ and $HET^4$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Within this embodiment of the invention is encompassed a compound of Formula Ia wherein $R^6$ is selected from the group consisting of:

(1) $C_{1-10}$alkyl, (2) $C_{2-10}$alkenyl, (3) $C_{3-10}$alkynyl, (4) $C_{3-6}$cycloalkyl and (5) phenyl, wherein items (1) to (3) above are each optionally substituted from one up to the maximum number of substituable positions with a substituent independently selected from the group consisting of: halo, hydroxy, $C_{3-6}$cycloalkyl, phenyl and $C_{1-3}$alkoxy, said $C_{3-6}$cycloalkyl, phenyl and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl and $C_{1-3}$alkoxy, said phenyl and $C_{1-3}$alkoxy groups optionally substituted from one up to the maximum number of substitutable positions with halo, and wherein item (5) above is optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo.

The invention also encompasses a compound of Formula Ia wherein n is 0, Y is a bond and $R^6$ is $C_{1-6}$alkyl.

The invention also encompasses a method of treating an immunoregulatory abnormality in a mammalian patient in need of such treatment comprising administering to said patient a compound of Formula I in an amount that is effective for treating said immunoregulatory abnormality.

Within this embodiment is encompassed the above method wherein the immunoregulatory abnormality is an autoimmune or chronic inflammatory disease selected from the group consisting of: systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

Also within this embodiment is encompassed the above method wherein the immunoregulatory abnormality is bone marrow or organ transplant rejection or graft-versus-host disease.

Also within this embodiment is encompassed the above method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also within this embodiment is encompassed the above method wherein the immunoregulatory abnormality is multiple sclerosis.

Also within this embodiment is encompassed the above method wherein the immunoregulatory abnormality is rheumatoid arthritis.

Also within this embodiment is encompassed the above method wherein the immunoregulatory abnormality is systemic lupus erythematosus.

Also within this embodiment is encompassed the above method wherein the immunoregulatory abnormality is psoriasis.

Also within this embodiment is encompassed the above method wherein the immunoregulatory abnormality is rejection of transplanted organ or tissue.

Also within this embodiment is encompassed the above method wherein the immunoregulatory abnormality is inflammatory bowel disease.

Also within this embodiment is encompassed the above method wherein the immunoregulatory abnormality is a malignancy of lymphoid origin including acute and chronic lymphocytic leukemias and lymphomas.

The invention also encompasses a method of suppressing the immune system in a mammalian patient in need of immunosuppression comprising administering to said patient an immunosuppressing effective amount of a compound of Formula I.

The invention also encompasses a pharmaceutical composition comprised of a compound of Formula I in combination with a pharmaceutically acceptable carrier.

The invention also encompasses a method of treating a respiratory disease or condition in a mammalian patient in need of such treatment comprising administering to said patient a compound of Formula I in an amount that is effective for treating said respiratory disease or condition. Within this embodiment is encompasses the above method wherein the respiratory disease or condition is selected from the group consisting of: asthma, chronic bronchitis, chronic obstructive pulmonary disease, adult respiratory distress syndrome, infant respiratory distress syndrome, cough, eosinophilic granuloma, respiratory syncytial virus bronchiolitis, bronchiectasis, idiopathic pulmonary fibrosis, acute lung injury and bronchiolitis obliterans organizing pneumonia.

In another embodiment, the invention encompasses a method of treating an immunoregulatory abnormality in a mammalian patient in need of such treatment comprising administering to said patient a compound which is an agonist of the $S1P_1$/Edg1 receptor in an amount effective for treating said immunoregulatory abnormality, wherein said compound possesses a selectivity for the $S1P_1$/Edg1 receptor over the $S1P_3$/Edg3 receptor of at least 5,000 fold as measured by the ratio of $EC_{50}$ for the $S1P_1$/Edg1 receptor to the $EC_{50}$ for the $S1P_3$/Edg3 receptor as evaluated in the $^{35}$S-GTPγS binding assay and wherein said compound possesses an $EC_{50}$ for binding to the $S1P_1$/Edg1 receptor of 100 nM or less as evaluated by the $^{35}$S-GTPγS binding assay.

Within this embodiment is encompassed the above method wherein the compound possesses an $EC_{50}$ for binding to the $S1P_1$/Edg1 receptor of 10 nM or less as evaluated by the $^{35}$S-GTPγS binding assay.

Also, within this embodiment is encompassed the above method wherein the compound possesses an $EC_{50}$ for binding to the $S1P_1$/Edg1 receptor of 1 nM or less as evaluated by the $^{35}$S-GTPγS binding assay.

Also, within this embodiment is encompassed the above method wherein the compound has a selectivity for the $S1P_1$/Edg1 receptor over the $S1P_3$/Edg3 receptor of at least 10,000 fold as measured by the ratio of $EC_{50}$ for the $S1P_1$/Edg1 receptor to the $EC_{50}$ for the $S1P_3$/Edg3 receptor as evaluated in the $35_{S\text{-}GTP\gamma}$S binding assay.

Also, within this embodiment is encompassed the above method wherein the compound has a selectivity for the $S1P_1$/Edg1 receptor over the $S1P_3$/Edg3 receptor of at least 15,000 fold as measured by the ratio of $EC_{50}$ for the $S1P_1$/Edg1 receptor to the $EC_{50}$ for the $S1PR_3$/Edg3 receptor as evaluated in the $^{35}$S-GTPγS binding assay.

Also, within this embodiment is encompassed the above method wherein the compound has a selectivity for the $S1P_1$/Edg1 receptor over the $S1P_3$/Edg3 receptor of at least 20,000 fold as measured by the ratio of $EC_{50}$ for the $S1P_1$/Edg1 receptor to the $EC_{50}$ for the $S1PR_3$/Edg3 receptor as evaluated in the $^{35}$S-GTPγS binding assay.

Also, within this embodiment is encompassed the above method wherein the patient also has a respiratory disease or condition.

Also, within this embodiment is encompassed the above method wherein the patient is also suffering from a cardiovascular disease or condition.

Exemplifying the invention are the following compounds:

| Example No. | Structure |
| --- | --- |
| 1 | 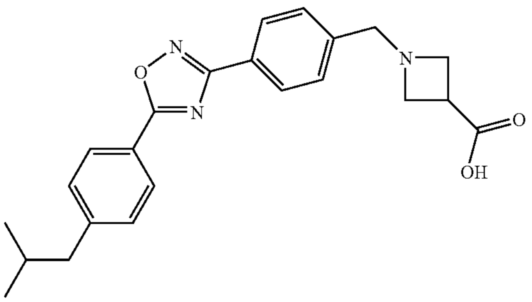 |
| 2 | 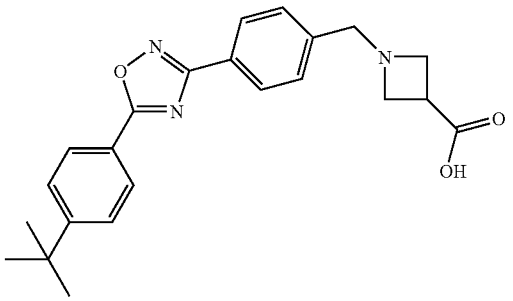 |
| 3 | 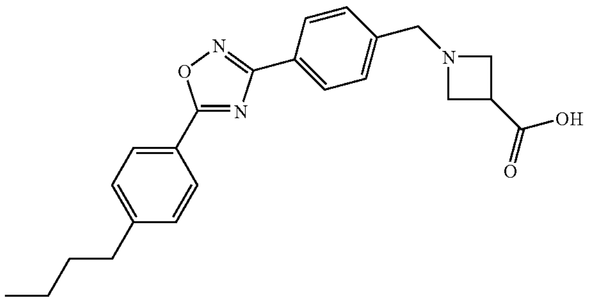 |
| 4 | 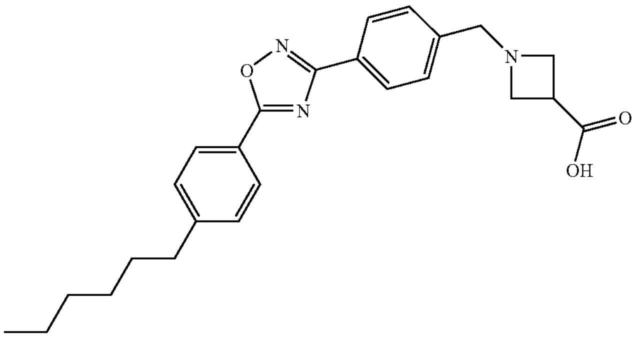 |

-continued
| Example No. | Structure |
| --- | --- |
| 5 | 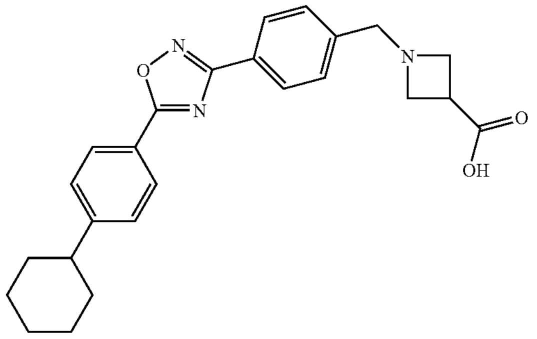 |
| 6 | 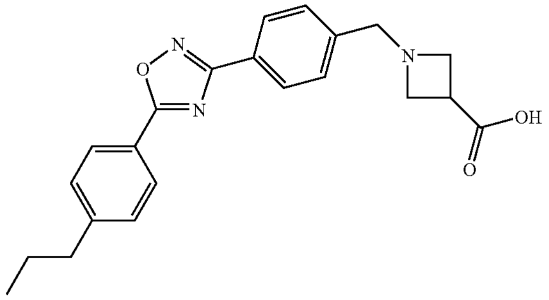 |
| 7 | 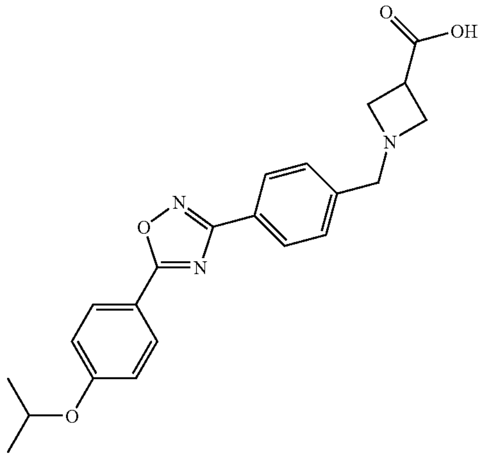 |
| 8 | 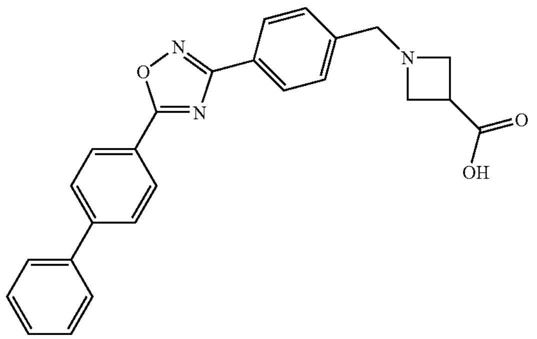 |

-continued
| Example No. | Structure |
| --- | --- |
| 9 | 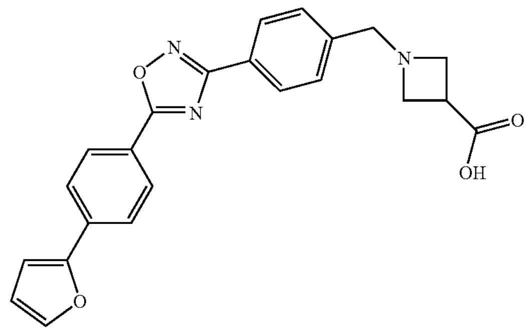 |
| 10 | 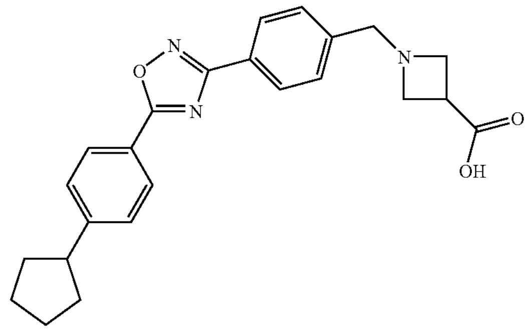 |
| 11 | 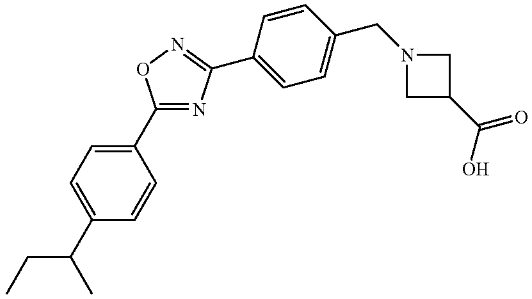 |
| 12 | 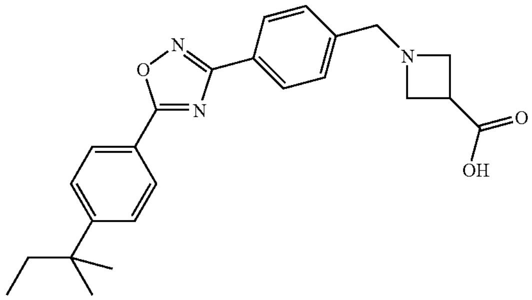 |
| 13 | 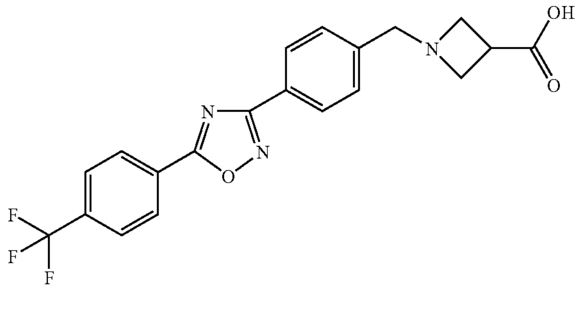 |

-continued
| Example No. | Structure |
| --- | --- |
| 15 | 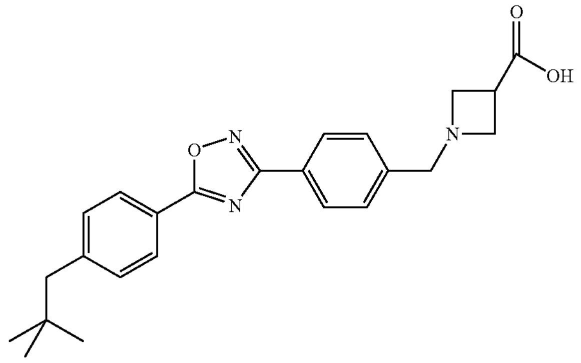 |
| 17 | 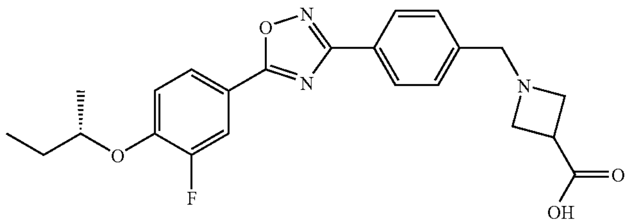 |
| 18 | 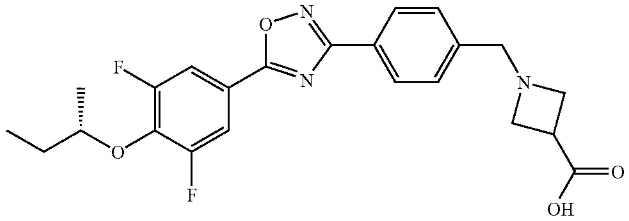 |
| 19 | 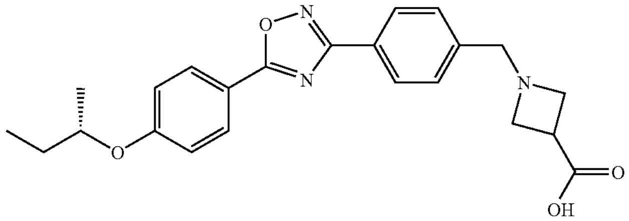 |
| 21 | 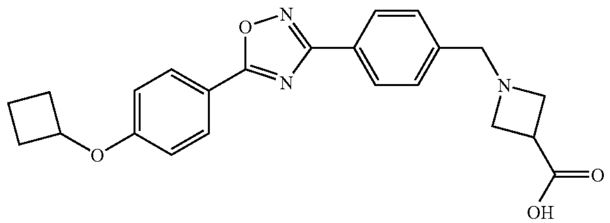 |

-continued
| Example No. | Structure |
| --- | --- |
| 22 | 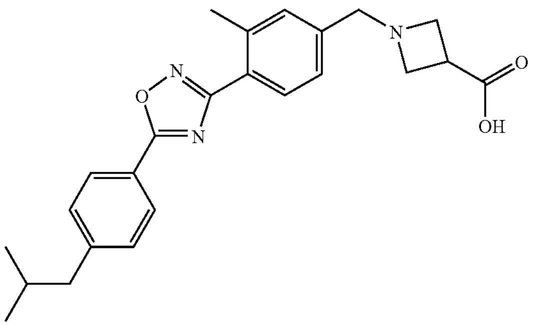 |
| 23 | 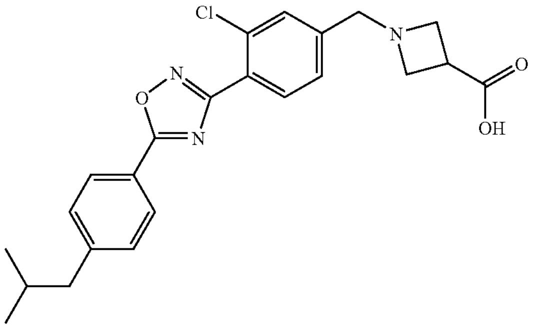 |
| 24 | 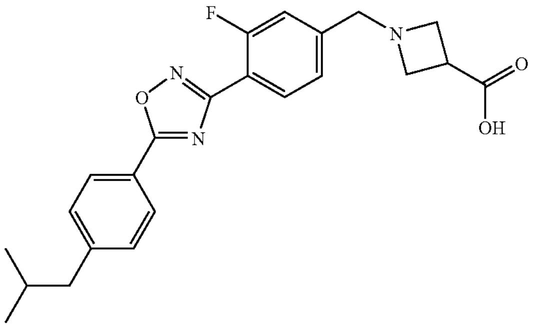 |
| 25 | 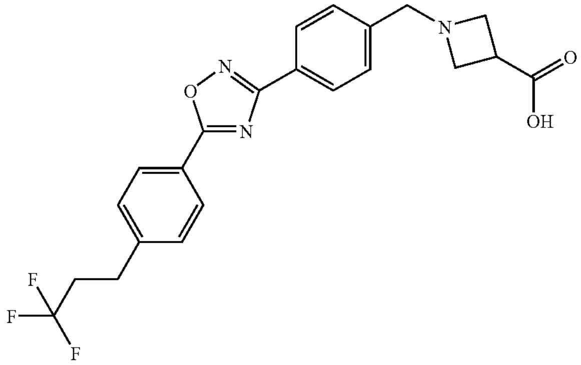 |

-continued
| Example No. | Structure |
|---|---|
| 26 | 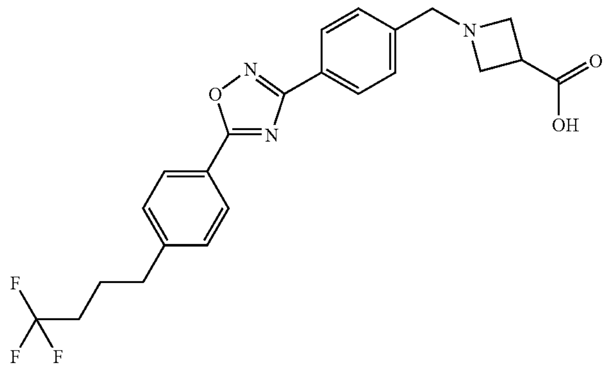 |
| 27 | 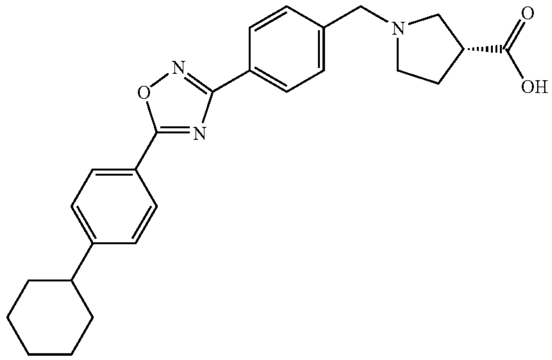 |
| 28 | 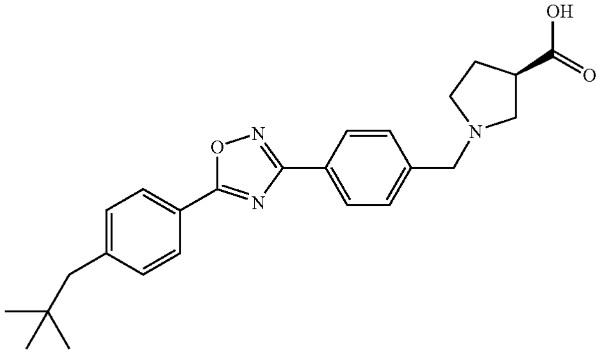 |
| 29 | 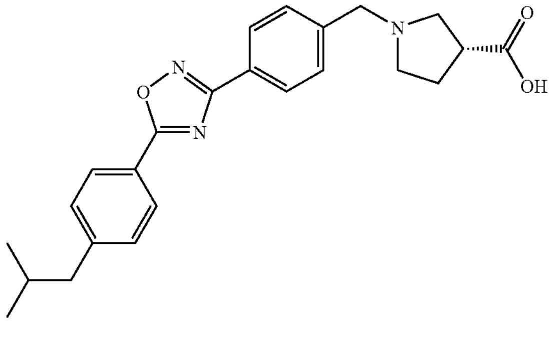 |

-continued

| Example No. | Structure |
|---|---|
| 30 | 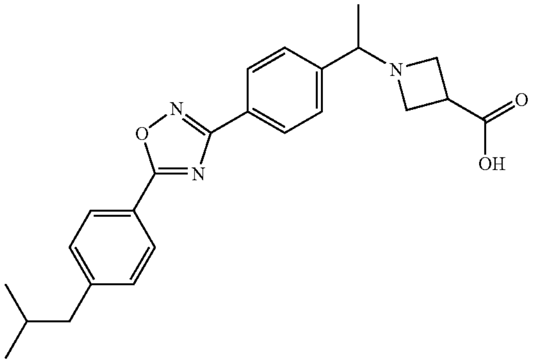 |

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes, propenyl, 1-methylethenyl, butenyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "treating" encompasses not only treating a patient to relieve the patient of the signs and symptoms of the disease or condition but also prophylactically treating an asymptomatic patient to prevent the onset or progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The invention described herein includes pharmaceutically acceptable salts and hydrates. Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

For purposes of this Specification, "pharmaceutically acceptable hydrate" means the compounds of the instant invention crystallized with one or more molecules of water to form a hydrated form.

The invention also includes the compounds falling within Formula I in the form of one or more stereoisomers, in substantially pure form or in the form of a mixture of stereoisomers. All such isomers are encompassed within the present invention.

By virtue of their $S1P_1$/Edg1 agonist activity, the compounds of the present invention are immunoregulatory agents useful for treating or preventing automimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also embodied within the present invention is a method of preventing or treating resistance to transplantation or transplantation rejection of organs or tissues in a mammalian patient in need thereof, which comprises administering a therapeutically effective amount of the compound of Formula I.

A method of suppressing the immune system in a mammalian patient in need thereof, which comprises administering to the patient an immune system suppressing amount of the compound of Formula I is yet another embodiment.

Most particularly, the method described herein encompasses a method of treating or preventing bone marrow or organ transplant rejection which is comprised of admininstering to a mammalian patient in need of such treatment or prevention a compound of Formula I, or a pharmaceutically acceptable salt or hydrate thereof, in an amount that is effective for treating or preventing bone marrow or organ transplant rejection.

The compounds of the present invention are also useful for treating a respiratory dieases or condition, such as asthma, chronic bronchitis, chronic obstructive pulmonary disease, adult respiratory distress syndrome, infant respiratory distress syndrome, cough, eosinophilic granuloma, respiratory syncytial virus bronchiolitis, bronchiectasis, idiopathic pulmonary fibrosis, acute lung injury and bronchiolitis obliterans organizing pneumonia Furthermore, the compounds of the present invention are selective agonists of the $S1P_1$/Edg1 receptor having selectivity over $S1P_3$/Edg3 receptor. An Edg1 selective agonist has advantages over current therapies and extends the therapeutic window of lymphocytes sequestration agents, allowing better tolerability with higher dosing and thus improving efficacy as monotherapy.

The present invention also includes a pharmaceutical formulation comprising a pharmaceutically acceptable carrier and the compound of Formula I or a pharmaceutically acceptable salt or hydrate thereof. A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506, rapamycin and FTY720.

The present compounds, including salts and hydrates thereof, are useful in the treatment of autoimmune diseases, including the prevention of rejection of bone marrow transplant, foreign organ transplants and/or related afflictions, diseases and illnesses.

The compounds of this invention can be administered by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1–2000 milligrams per day. Ordinarily, from 1 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Methods of Synthesis

Two general methods that can be employed to prepare compounds in the current invention are depicted in Scheme 1. Intermediates i may be available from commercial sources (e.g., azetidine-3-carboxylic acid where n=0) or they can be prepared according to published procedures (e.g., representative syntheses of pyrrolidine-3-(R)-carboxylic acid and pyrrolidine-3-(S)-carboxylic acid (n=1) are described by Gmeiner, O., et. al. in *Synthesis,* 1998, 1491). Combining i with aldehyde ii in the presence of an appropriate reducing agent (e.g., sodium cyanoborohydride, sodium triacetoxyborohydride, sodium borohydride) in a compatible solvent (e.g., methanol, ethanol, acetonitrile, methylene chloride) can afford compounds of Formula I. Alternatively, intermediates i can be combined with a benzyl halide or sulfonate ester iv in the presence of an appropriate base (e.g., sodium carbonate, potassium carbonate, triethylamine, N,N-diisopropylethylamine) in a compatible solvent solvent (e.g., methanol, ethanol, acetonitrile) at or above room temperature to give compounds of Formula I. In cases where a carboxylic acid in structure i would interfere with the transformation to the compound of Formula I, an appropriate protecting group (Greene & Wuts, eds., "Protecting Groups in Organic Synthesis", John Wiley & Sons, Inc.) that would mask the carboxylic acid and allow for its liberation after coupling with either ii or iv can be employed. In cases where Formula I contains asymmetric centers, the individual stereoisomers of Formula I can obtained by methods known to those skilled in the art which include (but are not limited to): stereospecific synthesis, resolution of salts of Formula I or any of the intermediates used in its preparation with enantiopure acids or bases, resolution of Formula I or any of the intermediates used in its preparation by HPLC employing enantiopure stationary phases.

Scheme 1

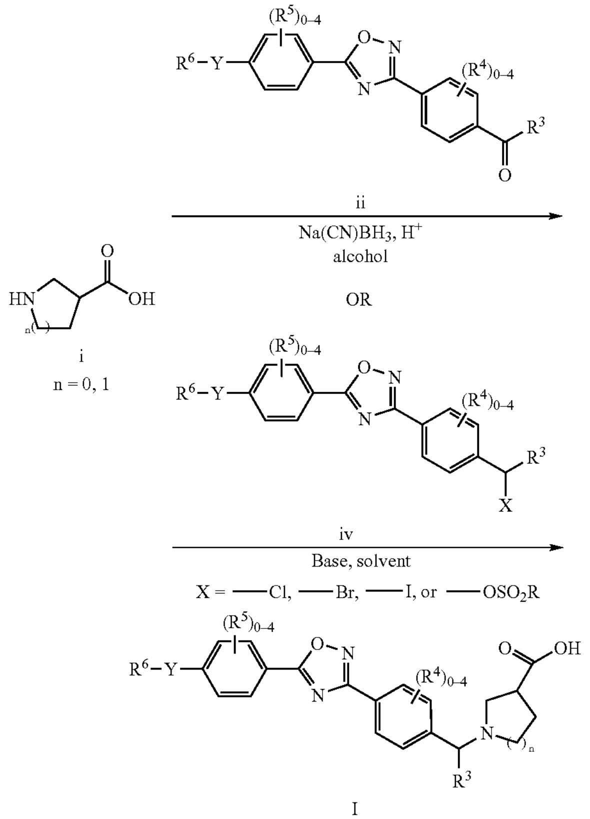

I n = 0, 1

Methods that can be used to prepare compounds that can be employed as intermediate ii in Scheme 1 above are shown in Scheme 2. Many benzonitriles v are commercially available and can be combined with hydroxylamine. HCl in the presence of a neutralizing base (e.g., triethylamine, sodium bicarbonate) in an appropriate solvent (methanol, ethanol, N,N-dimethyl formamide) at or above room temperature to afford N-hydroxy benzamidines vi. Benzoic acids vii can be activated with a carbodiimide (e.g. N,N'-dicyclohexylcarbodiimide, 1-(3-dimethylaminopropyl)-3-ethylcarbodiimide) and 1-(hydroxy)benzotriazole in an appropriate solvent (acetonitrile, THF, N,N-dimethyl formamide) and then treated with vi at or above room temperature to afford 1,2,4-oxadiazoles viii. An alternative method to activate the benzoic acid vii would be to convert it to the corresponding benzoyl chloride (e.g., by warming vii in the presence of thionyl chloride or by treating vii with oxalyl chloride and catalytic N,N-dimethyl formamide in a suitable solvent). Intermediate ii is then obtained by converting A in viii to an aldehyde ($R^3$=H) or ketone. If A is an alcohol, carboxylic acid ester, acetal, hemiacetal, nitrile or N-alkoxyl-N-alkyl carboxamides this can be done using methods known by those skilled in the art (see Larock, "Comprehensive Organic Transformations, A Guide to Functional Group Preparations", VCH Publishers, Inc.).

Scheme 2

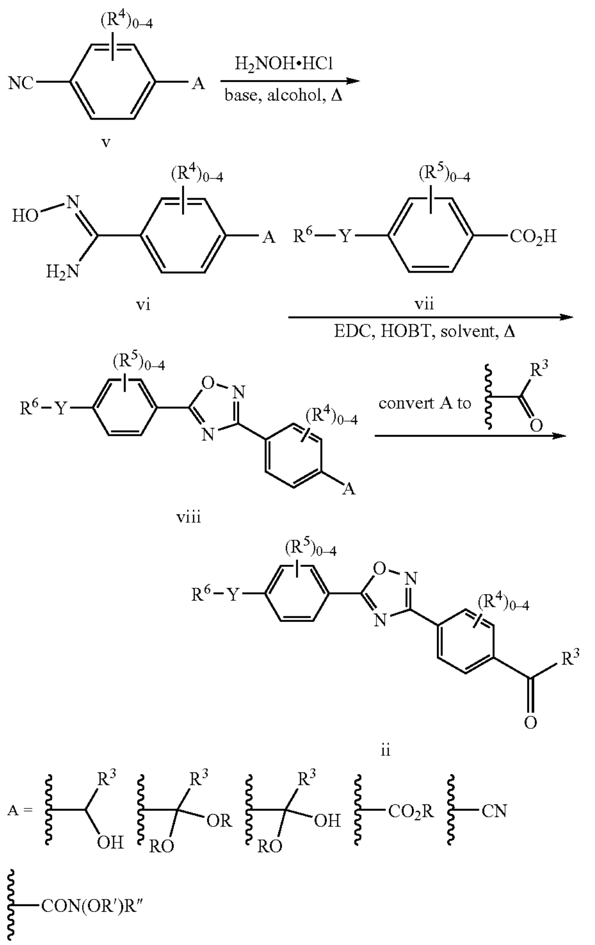

Many of the benzoic acids vii that can be used to prepare intermediates ii are available from commercial sources. Some methods that can be employed to prepare benzoic acids vii are depicted in Scheme 3. In cases where $R^6$ is alkyl and Y is —O—, phenol ix can be treated with an alkyl halide or alkyl sulfonate ester in the presence of base (e.g., triethylamine, sodium bicarbonate, potassium carbonate) in a suitable solvent (e.g., THF, acetonitrile, methanol, ethanol) at or above room temperature to afford ether x. Since a free carboxylic acid might interfere with this transformation, it may be desirable to use ix in which the carboxylate is masked as B (e.g., B could be a carboxylate ester, aldehyde, nitrile, etc.) which would then be subsequently transformed to a carboxylic acid using methods known to those skilled in the art (see Larock, "Comprehensive Organic Transformations, A Guide to Functional Group Preparations", VCH Publishers, Inc.). Alternative methods to prepare x (and therefore xi) could involve treating ix with an alcohol, triphenylphosphine and a dialkyl azodicarboxylate (e.g., diethyl azodicarboxylate or diisopropyl azodicarboxylate) in a suitable solvent (IBP, $CH_2Cl_2$, toluene) to give x. Another method to prepare x could be to treat aryl fluoride xii with an alcohol and a strong base (NaH, KH, lithium diisopropylamide) in a suitable solvent (THF, 1,2-dimethoxyethane) to give x. These methods would also be applicable if it were desirable to have any of $R^5$ be alkoxy.

There are many methods useful for preparing benzoic acids vii in which $R^6$ is alkyl and Y is a bond; one useful one is depicted in Scheme 3. Treating aryl bromide, iodide or triflate xiii with an alkyl magnesium bromide in the presence of a nickel catalyst in a suitable solvent (THF, 1,2-dimethoxyethane) can afford alkyl benzene xiv. Since a free carboxylic acid might interfere with this transformation, it may be desirable to use ix in which the carboxylate is masked as B (e.g., B could be nitrile, vinyl, aldehyde acetal, etc.) which would then be subsequently transformed to a carboxylic acid using methods known to those skilled in the art (see Larock, "Comprehensive Organic Transformations, A Guide to Functional Group Preparations", VCH Publishers, Inc.).

Methods for preparing the compounds of this invention are further illustrated in the following examples. Alternative routes will be easily discernible to practitioners in the field.

General

Concentration of solutions was carried out on a rotary evaporator under reduced pressure. Conventional flash chromatography was carried out on silica gel (230–400 mesh). Flash chromatography was also carried out using a Biotage Flash Chromatography apparatus (Dyax Corp.) on silica gel (32–63 mM, 60 Å pore size) in pre-packed cartridges of the size noted. NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) sat'd aqueous (sat'd), rt (rt), hour(s) (h), minute(s) (min).

HPLC Conditions

LC-1: Waters Xterra MS C18, 5μ, 4.6×50 mm column, 10:90 to 95:5 v/v $CH_3CN/H_2O$+0.05% TFA over 4.5 min, hold 1 min, PDA detection 200–600 nm, flow rate=2.5 mL/min.

LC-2: YMC-Pack Pro C18 S-5 μM 20×100 mm column or Kromasil KR100-10-C8 20×100 mm column; 10:90 to 90:10 v/v $CH_3CN/H_2O$+0.05% TFA over 12 min, hold 4 min, UV detection at either 220 or 254 nM, flow rate=10 mL/min.

Scheme 3

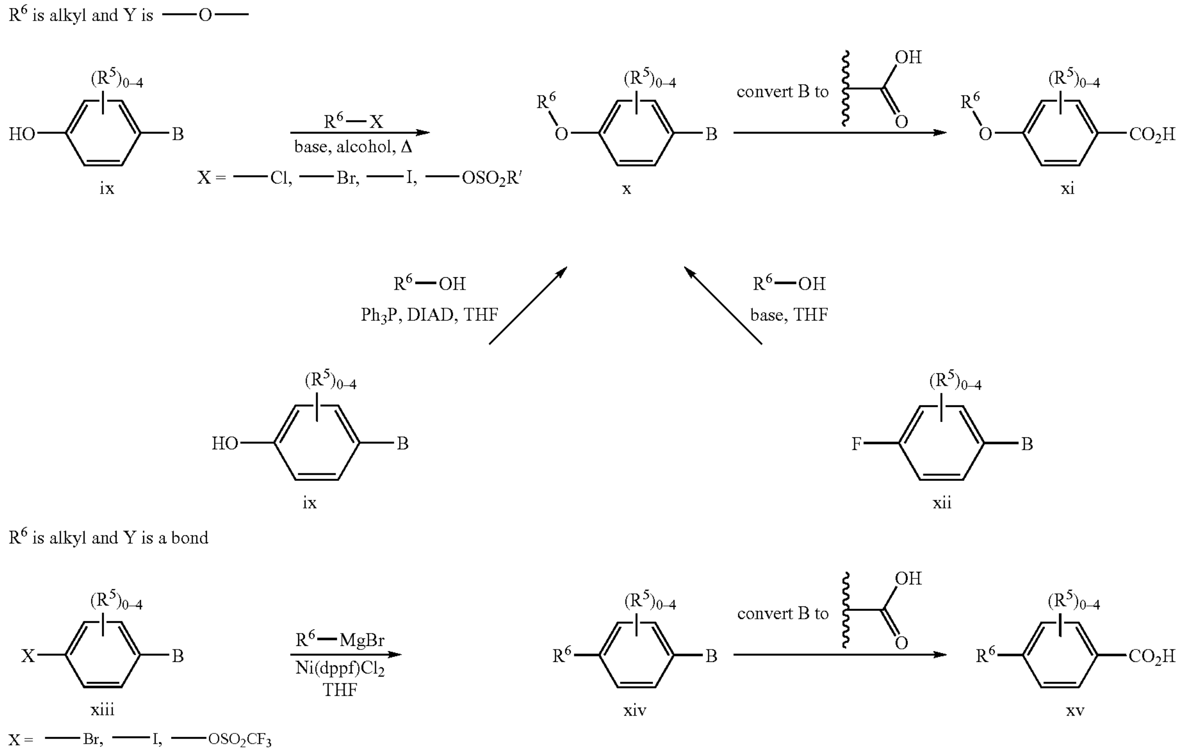

PREPARATION OF ALDEHYDE INTERMEDIATES

Aldehyde 1

4-(5-(4-(2-Methylpropyl)phenyl)-1,2,4-oxadiazol-3-yl)benzaldehyde

Step A: N-Hydroxy-4-(hydroxymethyl)benzamidine

A solution of 25.0 g (150 mmol) of 4-(hydroxymethyl) benzonitrile, 20.8 g (300 mmol) of hydroxyamine hydrochloride and 50.4 g (600 mmol) of sodium bicarbonate in 250 mL of methanol was heated to reflux and stirred for 20 h. The reaction mixture was cooled to rt and filtered. The solid was washed with 100 mL of methanol. The combined methanol solution was concentrated to dryness to afford 31.0 g (99%) of the title compound: $^1$H NMR (400 Mhz, $CD_3OD$) δ 4.63 (s, 2H), 7.39 (d, J=8.0, 2H), 7.62 (d, J=8.0, 2H).

Step B: 4-(5-(4-(2-Methylpropyl)phenyl)-1,2,4-oxadiazol-3-yl)phenylmethanol A solution of 10.0 g (56.2 mmol) of 4-(2-methylpropyl) benzoic acid, 10.8 g (56.2 mmol) of 1-(3-dimethylaminopropyl)-3-ethylcarbodiimide hydrochloride and 7.6 g (56.2 mmol) of 1-hydroxybenzotriazole hydrate in 70 mL of DMF was stirred at rt for 30 min. N-Hydroxy-4-(hydroxymethyl) benzamidine (9.3 g, 56.2 mmol, from Step A) was added to the reaction mixture at rt and the resulting slurry was stirred at 140° C. for additional 2 h. The reaction was cooled to rt and quenched with 50 mL of water. The aqueous layer was extracted with 200 mL of ethyl acetate. The organic layer was washed with 0.5 N HCl solution, saturated $NaHCO_3$ solution and water and then was concentrated to dryness to afford 16.5 g of the title compound: $^1$H NMR (400 Mhz, $CD_3OD$) δ 0.95 (d, J=6.7, 6H), 1.96 (m, 1H), 2.61 (d, J=7.3, 2H), 7.42 (d, J=8.0, 2H), 7.54 (d, J=8.2, 2H), 8.13 (m, 4H).

Step C: 4-(5-(4-(2-Methylpropyl)phenyl)-1,2,4-oxadiazol-3-yl)benzaldehyde

A solution of 9.8 mL (112.4 mmol) of oxalyl chloride in 300 mL of dichloromethane was treated with 12 mL (168.6 mmol) of DMSO at −78° C. To the reaction mixture, 16.5 g of 4-(5-(4-(2-methylpropyl)phenyl)-1,2,4-oxadiazol-3-yl) phenylmethanol (from Step B) was added followed by 78 mL (450 mmol) of N,N-diisopropylethylamine at −78° C. The reaction mixture was allowed to warm to rt over 1 h. Dichloromethane was removed under reduced pressure and the residue was partitioned between ethyl acetate and 0.5 N $KHSO_4$ solution. The organic layer was washed with 1 N HCl solution, saturated $NaHCO_3$ and water and then was concentrated to dryness. The crude product was recrystallized from hexanes to afford 11.9 g of the title compound: $^1$H NMR (400 Mhz) δ 0.97 (d, J=6.7, 6H), 1.97 (m, 1H), 2.61 (d, J=7.0, 2H), 7.37 (d, J=8.0, 2H), 8.06 (d, J=8.2, 2H), 8.16 (d, J=8.2, 2H), 8.39 (d, J=8.0, 2H), 10.14 (s, 1H); ESI-MS 307 (M+1H); LC-1: 4.5 min.

Aldehyde 2

4-(5-(4-Butylphenyl)-1,2,4-oxadiazol-3-yl)benzaldehyde

The title compound was prepared using a procedure analogous to Aldehyde 1 substituting 4-butylbenzoic acid for 4-(2-methylpropyl)benzoic acid in Step B: ESI-MS 307 (M+H); LC-1: 4.6 min.

Aldehyde 3

4-(5-(4-Hexylphenyl)-1,2,4-oxadiazol-3-yl)benzaldehyde

The title compound was prepared using a procedure analogous to Aldehyde 1 substituting 4-hexylbenzoic acid for 4-(2-methylpropyl)benzoic acid in Step B: ESI-MS 335 (M+H); LC-1: 5.0 min.

Aldehyde 4

4-(5-(4-Cyclohexylphenyl)-1,2,4-oxadiazol-3-yl) benzaldehyde

The title compound was prepared using a procedure analogous to Aldehyde 1 substituting 4-cyclohexylbenzoic acid for 4-(2-methylpropyl)benzoic acid in Step B: ESI-MS 333 (M+H); LC-1: 4.8 min.

Aldehyde 5

4-(5-(4-Propylphenyl)-1,2,4-oxadiazol-3-yl)benzaldehyde

The title compound was prepared using a procedure analogous to Aldehyde 1 substituting 4-propylbenzoic acid for 4-(2-methylpropyl)benzoic acid in Step B: ESI-MS 293 (M+H); LC-1: 4.4 min.

Aldehyde 6

4-(5-(4-Isopropoxyphenyl)-1,2,4-oxadiazol-3-yl) benzaldehyde

The title compound was prepared using a procedure analogous to Aldehyde 1 substituting 4-isopropoxybenzoic acid for 4-(2-methylpropyl)benzoic acid in Step B: ESI-MS 309 (M+H); LC-1: 4.0 min.

Aldehyde 7

4-(5-(1,1'-Biphen-4-yl)-1,2,4-oxadiazol-3-yl)benzaldehyde

The title compound was prepared using a procedure analogous to Aldehyde 1 substituting 1,1'-biphenyl-4-carboxylic acid for 4-(2-methylpropyl)benzoic acid in Step B: ESI-MS 327 (M+H); LC-1: 4.3 min.

Aldehyde 8

4-(5-(4-(2-Furyl)phenyl)-1,2,4-oxadiazol-3-yl)benzaldehyde

The title compound was prepared using a procedure analogous to Aldehyde 1 substituting 4-(2-furyl)benzoic acid for 4-(2-methylpropyl)benzoic acid in Step B: ESI-MS 317 (M+H); LC-1: 4.1 min.

Aldehyde 9

4-(5-(4-Cyclopentylphenyl)-1,2,4-oxadiazol-3-yl) benzaldehyde

The title compound was prepared using a procedure analogous to Aldehyde 1 substituting 4-cyclopentylbenzoic acid for 4-(2-methylpropyl)benzoic acid in Step B: ESI-MS 319 (M+H); LC-1: 4.6 min.

Aldehyde 10

(±)-4-(5-(4-(1-Methylpropyl)phenyl)-1,2,4-oxadiazol-3-yl)benzaldehyde

The title compound was prepared using a procedure analogous to Aldehyde 1 substituting (±)-4-(1-methylpropyl)benzoic acid for 4-(2-methylpropyl)benzoic acid in Step B: ESI-MS 307 (M+H); LC-1: 4.5 min.

Aldehyde 11

4-(5-(4-(1,1-Dimethylpropyl)phenyl)-1,2,4-oxadiazol-3-yl)benzaldehyde

The title compound was prepared using a procedure analogous to Aldehyde 1 substituting 4-(1,1-dimethylpropyl)benzoic acid for 4-(2-methylpropyl)benzoic acid in Step B: ESI-MS 321 (M+H); LC-1: 4.6 min.

Aldehyde 12

4-(5-(4-(1,1-Dimethylethyl)phenyl)-1,2,4-oxadiazol-3-yl)benzaldehyde

The title compound was prepared using a procedure analogous to Aldehyde 1 substituting 4-(1,1-dimethylethyl) benzoic acid for 4-(2-methylpropyl)benzoic acid in Step B: ESI-MS 307 (M+H); LC-1: 4.4 min.

Aldehyde 13

4-(5-(4-(Trifluoromethyl)phenyl)-1,2,4-oxadiazol-3-yl)benzaldehyde

The title compound was prepared using a procedure analogous to Aldehyde 1 substituting 4-(trifluoromethyl) benzoic acid for 4-(2-methylpropyl)benzoic acid in Step B: ESI-MS 319 (M+H); LC-1: 3.9 min.

Aldehyde 14

4-(5-(2,3-Dihydrobenzofuran-5-yl)-1,2,4-oxadiazol-3-yl)benzaldehyde

The title compound was prepared using a procedure analogous to Aldehyde 1 substituting 2,3-dihydrobenzofuran-5-carboxylic acid for 4-(2-methylpropyl)benzoic acid in Step B: ESI-MS 293 (M+H); LC-1: 3.5 min.

Aldehyde 15

4-(5-(4-(2,2-Dimethylpropyl)phenyl)-1,2,4-oxadiazol-3-yl)benzaldehyde

Step A: 4-(2,2-Dimethylpropyl)4-ethenylbenzene

To a solution of 0.8 g (33.10 mmol) of magnesium turnings and 2.0 g (13.2 mmol) of 1-bromo-2,2-dimethylpropane in 10 mL diethyl ether was added a solution of 1.42 g (7.76 mmol) of 4-bromostyrene and 69 mg (0.13 mmol) of $Ni(dppf)Cl_2$ The resulting reaction mixture was heated at refluc for 8 h. The reaction was quenched with 50% saturated $NH_4Cl$, and was extracted with MTBE (2×150 mL). The combined extractions were washed with water, dried and concentrated. Flash chromatography on a Biotage 40M cartridge with hexanes as the eluant afforded 1.74 g of the title compound: $^1$H NMR (500 Mhz) δ 0.93 (s, 9H), 2.49 (s, 2H), 5.20 (d, J=10.9, 1H), 5.73 (d, J=17.6, 1H), 6.72 (dd, $J_1$=17.6, $J_2$=10.8, 1H), 7.10 (d, J=8.2, 2H), 7.33 (d, J=8.0, 2H); ESI-MS 161 (M+H); LC-1: 4.4 min.

Step B: 4-(2,2-Dimethylpropyl)benzoic acid

To a solution of 1.74 g (7.76 mmol) of 4-(2,2-dimethylpropyl)-4-ethenylbenzene (from Step A) in 10 mL EtOAc and 10 mL $H_2O$ was added 8.30 g (38.8 mmol) of $NaIO_4$ and 1 mg (0.0078 mmol) $RuO_2$. The reaction mixture was heated to 40° C. for 30 min. The reaction mixture was cooled and stirred at rt for 16 hr. To the reaction mixture was added $H_2O$ and EtOAc, and layers were separated. The organic layer was dried and concentrated to dryness to provide 776 mg of the title compound: $^1$H NMR (500 Mhz) δ 0.91 (s, 9H), 2.53 (s, 2H), 7.12 (d, J=8.0, 2H), 7.84 (d, J=8.0, 2H); ESI-MS 193 (M+H); LC-1: 3.2 min.

Step C: 4-(5-(4-(2,2-Dimethylpropyl)phenyl)-1,2,4-oxadiazol-3-yl)benzaldehyde

The title compound was prepared using a procedure analogous to Aldehyde 1 substituting 4-(2,2-dimethylpropyl)benzoic acid (from Step B above) for 4-(2-methylpropyl)benzoic acid in Aldehyde 1, Step B: ESI-MS 321 (M+H); LC-1: 4.7 min.

Aldehyde 16

4-(5-(4-(3,3,3-Trifluoropropyl)phenyl)-1,2,4-oxadiazol-3-y)benzaldehyde

The title compound was prepared using procedures analogous to those described for Aldehyde 15 substituting 1-bromo-3,3,3-trifluoropropane for 1-bromo-2,2-dimethylpropane in Step A: ESI-MS 347 (M+H); LC-1: 4.0 min.

Aldehyde 17

4-(5-(4-(3,3,3-Trifluorobutyl)phenyl)-1,2,4-oxadiazol-3-y)benzaldehyde

The title compound was prepared using procedures analogous to those described for Aldehyde 15 substituting 1-bromo-3,3,3-trifluorobutane for 1-bromo-2,2-dimethylpropane in Step A: ESI-MS 361 (M+H); LC-1: 4.5 min.

Aldehyde 18

4-(5-(4-(2-Methylpropyl))-1,2,4-oxadiazol-3-yl)-3-methylbenzaldehyde

Step A: 3-(4-Bromo-2-methylphenyl)-5-(4-(2-methylpropyl)phenyl)-1,2,4-oxadiazole The title compound was prepared using a procedure analogous to described to prepare 4-(5-(4-(2-methylpropyl) phenyl)-1,2,4-oxadiazol-3-yl)phenylmethanol (Aldehyde 1, Step B) substituting N-hydroxy-(4-bromo-2-methyl)benzamidine for N-hydroxy-(4-hydroxymethyl)benzamidine: $^1$H NMR (400 Mhz, $CCl_3D$) δ 0.98 (d, J=6.6, 6H), 1.98 (m, 1H), 2.62 (d, J=7.1, 2H), 2.72 (s, 3H), 7.37 (d, J=8.1, 2H), 7.52 (d, J=8.4, 1H), 7.56 (s, 1H), 8.02 (d, J=8.4, 1H), 8.16 (d, J=8.1, 2H); ESI-MS 371 (M+H); LC-1: 5.3 min.

Step B: 4-(5-(4-(2-Methylpropyl)phenyl)-1,2,4-oxadiazol-3-yl)-3-methyl benzonitrile A solution of 2.3 g (6.2 mmol) of 3-(4-bromo-2-methylphenyl)-5-(4-(2-methylpropyl)phenyl)-1,2,4-oxadiazole (from Step A), 1.46 g (12.4 mmol) of zinc cyanide and 2.15 g (1.86 mmol) of $Pd(PPh_3)_4$ in 20 mL of DMF was stirred at 100° C. for 20 h. The reaction was cooled and quenched with 10 mL of sat'd $NaHCO_3$. The quenched mixture was extracted with 100 mL of dichloromethane. The extract was dried and concentrated to afford 1.40 g of the title compound which was used without further purification: ESI-MS 318 (M+H); LC-1: 4.8 min.

Step C: 4-(5-(4-(2-Methylpropyl)phenyl)-1,2,4-oxadiazol-3-yl)-3-methyl benzaldehyde A solution of 1.40 g (4.4 mmol) of 4-(5-(4-(2-methylpropyl)phenyl)-1,2,4-oxadiazol-3-yl)-3-methyl benzonitrile (from Step B) in 20 mL of toluene was treated with 8.8 mL (8.8 mmol) of DIBALH (1.0 M in dichloromethane) at −78° C. The resulting mixture was stirred at −78° C. for 30 min and quenched with 0.3 mL of acetic acid and 5 mL of water. The quenched mixture was allowed to warm to rt and was extracted with 50 mL of ethyl acetate. The extract was dried and concentrated to afford 1.0 g of the title compound: ESI-MS 321 (M+H); LC-1: 4.7 min.

Aldehyde 19

4-(5-(4-(2-Methylpropyl)phenyl)-1,2,4-oxadiazol-3-yl)-3-chlorobenzaldehyde

The title compound was prepared using procedures analogous to those described for Aldehyde 19 substituting N-hydroxy-(4-bromo-2-chloro)benzamidine for N-hydroxy-(4-bromo-2-methyl)benzamidine in Step A: ESI-MS 341 (M+H); LC-1: 4.6 min.

Aldehyde 20

4-(5-(4-(2-Methylpropyl)phenyl)-1,2,4-oxadiazol-3-yl)-3-fluorobenzaldehyde

The title compound was prepared using procedures analogous to those described for Aldehyde 19 substituting N-hydroxy-(4-bromo-2-fluoro)benzamidine for N-hydroxy-(4-bromo-2-methyl)benzamidine in Step A: ESI-MS 325 (M+H); LC-1: 4.4 min.

Aldehyde 21

4-(5-(4-(2-(S)-Butoxy)-3-trifluoromethylphenyl)-1,2,4-oxadiazol-3-yl)benzaldehyde Step A: 3-Trifluoromethyl-4-(2-(S)-butoxy)benzonitrile A solution of 1.1 g (5.9 mmol) of 4-fluoro-3-trifluoromethylbenzonitrile and 485 mg (6.5 mmol) of (S)-(+)-2-butanol in 10 mL of THF at −10° C. was treated with 235 mg (5.9 mmol) of sodium hydride. The resulting mixture was stirred cold for 2 h, then quenched with 10 mL of $H_2O$. The quenched solution was extracted with 30 mL of $Et_2O$, dried over $MgSO_4$ and concentrated. Chromatography on a Biotage 40M cartridge using 4:1 v/v hexanes/EtOAc as the eluant afforded 550 mg of the title compound: $^1H$ NMR (500 Mhz) δ 0.99 (t, J=7.6, 3H), 1.35 (d, J=6.2, 3H), 1.58–1.83 (m, 2H), 4.51 (septet, 1H), 7.04 (d, J=8.7, 1H), 7.75 (d, J=8.7, 1H), 7.85 (s, 1H).

Step B: 3-Trifluoromethyl-4-(2-(S)-butoxy)benzoic acid

A solution of 550 mg (2.2 mmol) of 3-trifluoromethyl-4-(2-(S)-methylpropyloxy)benzonitrile (from Step A) in 5 mL of EtOH was treated with 1.5 mL of 5.0 N NaOH and was heated to 80° C. for 3 h. The reaction was then concentrated, treated with 2 N HCl, extracted with 30 mL of EtOAc, dried over $MgSO_4$ and concentrated which afforded 600 mg of the title compound: $^1H$ NMR (500 Mhz) δ 0.99 (t, J=7.3, 3H), 1.43 (d, J=5.9, 3H), 1.73–1.83 (m, 2H), 4.54 (septet, 1H), 7.02 (d, J=8.9, 1H), 8.21 (d, J=8.9, 1H), 8.32 (s, 1H).

Step C: 4-(5-(4-(2-(S)-Butoxy)-3-trifluoromethylphenyl)-1,2,4-oxadiazol-3-yl)phenylmethanol A solution of 600 mg (2.2 mmol) of 3-trifluoromethyl-4-(2-(S)-methylpropyloxy)benzoic acid (from Step B), 542 mg (2.2 mmol) of EDC and 357 mg (2.2 mmol) of HOBT in 6 mL of DMF were stirred at rt for 1 h. The reaction was subsequently treated with 350 mg (2.2 mmol) of N-hydroxy-4-(hydroxymethyl)benzamidine (from Aldehyde 1, Step A) and heated to 80° C. for 12 h. The reaction mixture was cooled and purified via chromatography on a Biotage 40M cartridge using 2:1 v/v hexanes/EtOAc as the eluant affording 510 mg of the title compound: $^1H$ NMR (500 MHz) δ 1.01 (t, J=7.3, 3H), 1.38 (d, J=5.9, 3H), 1.73–1.83 (m, 2H), 4.55 (septet, 1H), 4.79 (s, 2H), 7.12 (d, J=8.9, 1H), 7.51 (d, J=8.2, 2H), 8.15 (d, J=8.2, 2H), 8.30 (d, J=8.9, 1H), 8.43 (s, 1H).

Step D: 4-(5-(4-(2-(S)-Butoxy)-3-trifluoromethylphenyl)-1,2,4-oxadiazol-3-yl)benzaldehyde A mixture of 510 mg (1.3 mmol) of 4-(5-(4-(2-(S)-methylpropyloxy)-3-trifluoromethylphenyl)-1,2,4-oxadiazol-3-yl)phenylmethanol (from Step C), 153 mg (1.3 mmol) of 4-methylmorpholine N-oxide and 510 mg of 4 A molecular sieves in 8 mL of $CH_3CN$ was treated with 13 mg (0.04 mmol) of tetrapropylammonium perruthnate and the resulting mixture was stirred ar rt for 2 h. The solids were filtered and the filtrate was concentrated. Chromatography on a Biotage 40 S cartridge using 9:1 v/v hexanes/EtOAc (1 L) as the eluant afforded 330 mg of the title compound: $^1H$ NMR (500 Mhz) δ 1.01 (t, J=7.3, 3H), 1.38 (d, J=5.9, 3H), 1.73–1.83 (m, 2H), 4.56 (sextet, 1H), 7.14 (d, J=8.9, 1H), 8.02 (d, J=8.2, 2H), 8.30 (d, J=8.2, 2H), 8.32 (d, J=8.9, 1H), 8.44 (s, 1H), 10.1 (s, 1H).

Aldehyde 22

4-(5-(4-(2-(S)-Butoxy)-3-fluorophenyl)-1,2,4-oxadiazol-3-yl)benzaldehyde

Step A: 3-Fluoro-4-(2-(S)-butoxy)benzaldehyde

A solution of 750 mg (5.4 mmol) of 3-fluoro-4-hydroxybenzaldehyde, 403 mg (5.4 mmol) of (R)-(−)-2-butanol and 2 g (7.5 mmol) triphenylphosphine in 10 mL of THF was treated with 1.5 mL of diisopropylazodicarboxylate. The resulting solution was stirred at rt for 14 h, cooled to rt and concentrated. Chromatography on a Biotage 40M cartridge using 4:1 v/v hexanes/$Et_2O$ as the eluant afforded 130 mg of the title compound: $^1$H NMR (500 Mhz) δ 0.99 (t, J=7.6, 3H), 1.35 (d, J=6.2, 3H), 1.58–1.83 (m, 2H), 4.47 (m, 1H), 7.05 (t, J=8.2, 1H), 7.59 (d, J=8.2, 1H), 7.61 (s, 1H), 9.84 (s, 1H).

Step B: 3-Fluoro-4-(2-(S)-butoxy)benzoic acid

A solution of 130 mg (0.66 mmol) of 3-fluoro-4-(2-(S)-butoxy)benzaldehyde in 1 mL of acetone was treated with a 73 mg (0.73 mmol) of chromium (VI) oxide in a 3:1 v/v mixture of water/sulfuric acid at 0° C. The reaction was allowed to warm to rt and was stirred for 2 hr then extracted with 10 mL of EtOAc, washed with brine, dried over $MgSO_4$ and concentrated to afford 130 mg of the title compound: $^1$H NMR (500 Mhz) δ 1.00 (t, J=7.6, 3H), 1.36 (d, J=6.2, 3H), 1.70 (m, 1H), 1.82 (m, 1H), 4.44 (m, 1H), 6.99 (t, J=8.2, 1H), 7.79 (d, J=8.2, 1H), 7.85 (s, 1H).

Step C: 4-(5-(4-(2-(S)-Butoxy)-3-fluorophenyl)-1,2,4-oxadiazol-3-yl)benzaldehyde The title compound was prepared using procedures analogous to those described for Aldehyde 21, Steps C and D substituting 3-fluoro-4-(2-(S)-butoxy)benzoic acid (from Step B) for 3-trifluoromethyl-4-(2-(S)-butoxy)benzoic acid in Aldehyde 21, Step C.

Aldehyde 23

4-(5-(4-(2-(S)-Butoxy)-3,5-difluorophenyl)-1,2,4-oxadiazol-3-yl)benzaldehyde

Step A: 1-Bromo-3,5-difluoro-4-(2-(S)-butoxy)benzene

The title compound was prepared using procedure analogous to that described in Aldehyde 22, Step A substituting 4-bromo-2,6-difluorophenol for 3-fluoro-4-hydroxybenzaldhyde.

Step B: 3,5-Difluoro-4-(2-(S)-butoxy)benzonitrile

A solution of 400 mg (1.5 mmol) of 1-bromo-3,5-difluoro-4-(2-(S)-butoxy)benzene (from Step A), 106 mg (0.9 mmol) of zinc cyanide, 69 mg of tris(dibenzylideneacetone) dipalladium(0) and 100 mg (0.18 mmol) of 1,1'-bis(diphenylphosino)ferrocene in 3 mL of DMF and 30 μL of water. The resulting solution was heated to 80° C. for 1 h and then cooled and concentrated. Chromatography on a Biotage 40M cartridge using 20:1 v/v hexanes/EtOAc as the eluant afforded 280 mg of the title compound: $^1$H NMR (500 Mhz) δ 1.01 (t, J=7.6, 3H), 1.35 (d, J=6.2, 3H), 1.68 (m, 1H), 1.79 (m, 1H), 4.47 (m, 1H), 7.25 (d, 2H).

Step C, 3,5-Difluoro-4-(2-(S)-butoxy)benzoic acid

The title compound was prepared using procedure analogous to that described in Aldehyde 21, Step B substituting 3,5-difluoro-4-(2-(S)-butoxy)benzonitrile (from Step B) for 3-trifluoromethyl-4-(2-(S)-butoxy)benzonitrile: $^1$H NMR (500 Mhz) δ 1.0 (t, J=7.3, 3H), 1.32 (d, J=5.9, 3H), 1.68 (m, 1H), 1.79 (m, 1H), 4.45 (m, 1H), 7.65 (d, J=8.3, 2H).

Step D: 4-(5-(4-(2-(S)-Butoxy)-3,5-di-fluorophenyl)-1,2,4-oxadiazol-3-yl)benzaldehyde The title compound was prepared using procedures analogous to those described for Aldehyde 21, Steps C and D substituting 3,5-difluoro-4-(2-(S)-butoxy)benzoic acid (from Step C) for 3-trifluoromethyl-4-(2-(S)-butoxy)benzoic acid in Aldehyde 21, Step C.

Aldehyde 24

4-(5-(4-(2-(S)-Butoxy)phenyl)-1,2,4-oxadiazol-3-yl)benzaldehyde

Step A: Methyl 4-(2-(S)-butoxy)benzoate

The title compound was prepared using procedure analogous to that described in Aldehyde 22, Step A substituting methyl 4-hydroxybenzoate for 3-fluoro-4-hydroxybenzaldehyde.

Step B: 4-(2-(S)-Butoxy)benzoic acid

A solution of 1.0 g (4.8 mmol) of methyl 4-(2-(S)-butoxy)benzoate in 15 mL of MeOH was treated with 1 mL of 5.0 N NaOH at rt for 1 h. The solution was concentrated, acidified with 6 mL of 2 N HCl, extracted with EtOAc, dried over $MgSO_4$ and concentrated to afford 800 mg (86%) of the title compound.

Step C: 4-(5-(4-(2-(S)-Butoxy)phenyl)-1,24-oxadiazol-3-yl)benzaldehyde

The title compound was prepared using procedures analogous to those described for Aldehyde 21, Steps C and D substituting 4-(2-(S)-butoxy)benzoic acid (from Step B) for 3-trifluoromethyl-4-(2-(S)-butoxy)benzoic acid in Aldehyde 21, Step C.

Aldehyde 25

4-(5-(4-(2-(R)-Butoxy)phenyl)-1,2,4-oxadiazol-3-yl)benzaldehyde

The title compound was prepared using procedures analogous to those described for Aldehyde 24 substituting 2-(S)-butanol for 2-(R)-butanol in Step A.

Aldehyde 25

4-(5-(4-(Cyclobutoxy)phenyl)-1,2,4-oxadiazol-3-yl)benzaldehyde

The title compound was prepared using procedures analogous to those described for Aldehyde 24 substituting cyclobutanol for 2-(R)-butanol in Step A.

PREPARATION OF EXAMPLES

Example 1

1-(4-(5-(4-(2-Methylpropyl)phenyl)-1,2,4-oxadiazol-3-yl)benzyl)azetidine-3-carboxylic acid A solution of 3.06 g (10.0 mmol) of Aldehyde 1, 1.06 g (10.5 mmol) of 3-azetidine carboxylic acid and 5 mL of acetic acid in 150 mL of methanol was stirred for 20 min at rt. A solution of sodium cyanoborohydride (380 mg, 5.0 mmol) in 20 mL of methanol was added. The reaction mixture was stirred for 1 h then was filtered. The solids were washed with 30 ml of methanol and dried to afford 2.88 g (74%) of the title compound: $^1H$ NMR (400 Mhz, $CD_3OD$) δ 0.95 (d, J=6.6, 6H), 1.96 (m, 1H), 2.62 (d, J=7.3, 2H), 3.42 (m, 1H), 4.19 (m, 4H), 4.41 (s, 2H), 7.43 (d, J=8.0, 2H), 7.64 (d, J=8.2, 2H), 8.14 (d, J=8.0, 2H), 8.23 (d, J=8.2, 2H); ESI-MS 392 (M+H); LC-1: 3.0 min.

Example 2

1-(4-(5-(4-(1,1-Dimethylethyl)phenyl)-1,2,4-oxadiazol-3-yl)benzyl)azetidine-3-carboxylic acid A solution of 103.7 mg (0.34 mmol) Aldehyde 12 and 37.7 mg (0.37 mmol) of azetidine-3-carboxylic acid was stirred at rt for 15 min and then was treated with 86.5 mg (0.408 mmol) of sodium triacetoxyborohydride. The reaction mixture was stirred at rt for 1 h. The reaction mixture was diluted with MeOH and directly purified by LC-2 to afford the title compound: $^1H$ NMR (500 Mhz) δ 1.38 (s, 9H), 3.65–3.72 (m, 1H), 4.32–4.39 (m, 4H), 4.50 (s, 2H), 7.64–7.68 (m, 4H), 8.13–8.16 (m, 2H), 8.24–8.25 (m, 2H); ESI-MS 392 (M+H); LC-1: 2.9 min.

The following Examples were prepared using a procedure analogous to that described for Example 2 substituting the appropriate Aldehyde for Aldehyde 12.

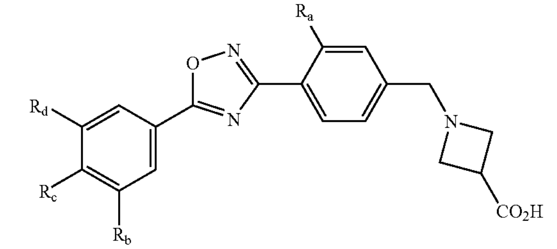

| Ex. | Aldehyde | $R_a$, $R_b$, $R_d$ | $R_c$ | ESI-MS (M + H) | LC-1 (min) |
|---|---|---|---|---|---|
| 3 | 2 | $R_a$=$R_b$=$R_d$=H | $CH_3$—$(CH_2)_3$— | 392 | 3.0 |
| 4 | 3 | $R_c$=$R_c$=$R_d$=H | $CH_3$—$(CH_2)_5$— | 420 | 3.3 |
| 5 | 4 | $R_a$=$R_b$=$R_d$=H | 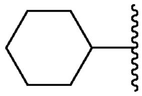 | 418 | 3.3 |
| 6 | 5 | $R_a$=$R_b$=$R_d$=H | $CH_3$—$(CH_2)_2$— | 378 | 2.8 |
| 7 | 6 | $R_a$=$R_b$=$R_d$=H | $(CH_3)_2CHO$— | 394 | 2.6 |
| 8 | 7 | $R_a$=$R_b$=$R_d$=H | 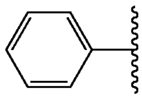 | 412 | 2.9 |
| 9 | 8 | $R_a$=$R_b$=$R_d$=H | 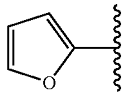 | 402 | 2.7 |
| 10 | 9 | $R_a$=$R_b$=$R_d$=H | 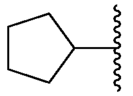 | 404 | 3.1 |

-continued

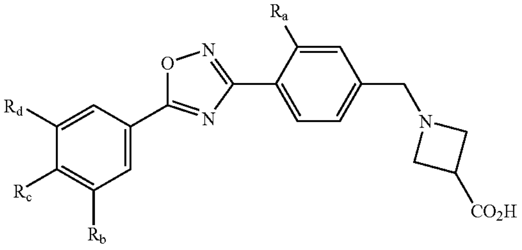

| Ex. | Aldehyde | $R_a$, $R_b$, $R_d$ | $R_c$ | ESI-MS (M + H) | LC-1 (min) |
|---|---|---|---|---|---|
| 11 | 10 | $R_a$=$R_b$=$R_d$=H | $CH_3CH_2CH(CH_3)$— | 392 | 3.0 |
| 12 | 11 | $R_a$=$R_b$=$R_d$=H | $CH_3CH_2C(CH_3)_2$— | 406 | 3.1 |
| 13 | 13 | $R_a$=$R_b$=$R_d$=H | $CF_3$— | 404 | 2.6 |
| 15 | 15 | $R_a$=$R_b$=$R_d$=H | $(CH_3)_3CCH_2$— | 406 | 3.2 |
| 17 | 22 | $R_a$=$R_d$=H $R_b$=F | (S)- $CH_3CH_2CH(CH_3)O$— | 426 | 3.5 |
| 18 | 23 | $R_a$=H $R_b$=$R_d$=F | (S)- $CH_3CH_2CH(CH_3)O$— | 444 | 3.6 |
| 19 | 24 | $R_a$=$R_b$=$R_d$=H | (S)- $CH_3CH_2CH(CH_3)O$— | 408 | 3.4 |
| 20 | 25 | $R_a$=$R_b$=$R_d$=H | (R)- $CH_3CH_2CH(CH_3)O$— | 408 | 3.4 |
| 21 | 26 | $R_a$=$R_b$=$R_d$=H | 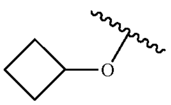 | 406 | 3.3 |
| 22 | 18 | $R_a$=$CH_3$ $R_b$=$R_d$=H | $(CH_3)_2CHCH_2$— | 406 | 3.2 |
| 23 | 19 | $R_a$=Cl $R_b$=$R_d$=H | $(CH_3)_2CHCH_2$— | 426 | 3.1 |
| 24 | 20 | $R_a$=F $R_b$=$R_d$=H | $(CH_3)_2CHCH_2$— | 410 | 3.1 |
| 25 | 16 | $R_a$=$R_b$=$R_d$=H | $CF_3CH_2CH_2$— | 432 | 3.3 |
| 26 | 17 | $R_a$=$R_b$=$R_d$=H | $CF_3CH_2CH_2CH_2$— | 446 | 3.4 |

The following Examples were prepared using a procedure analogous to that described for Example 2 substituting the appropriate Aldehyde for Aldehyde 1 and substituting pyrrolidine-3-(R)-carboxylic acid (*Synthesis,* 1998, 1491) for azetidine-3-carboxylic acid.

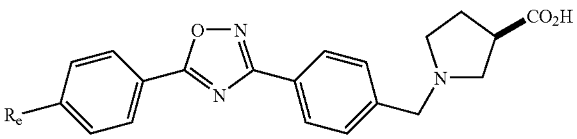

| Example | Aldehyde | $R_e$ | ESI-MS (M + H) | LC-1 (min) |
|---|---|---|---|---|
| 27 | 4 | 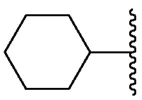 | 432 | 3.3 |
| 28 | 15 | $(CH_3)_3CCH_2$— | 420 | 3.3 |
| 29 | 1 | $(CH_3)_2CHCH_2$— | 406 | 3.0 |

Example 30

(±)-1-(1-(4-(5-(4-(2-Methylpropyl)phenyl)-1,2,4-oxadiazol-3-yl)phenyl)ethyl)azetidine-3-carboxylic acid Step A: (±)-4-(5-(4-(2-Methylpropyl)phenyl)-1,2,4-oxadiazol-3-yl)-1-(1-hydroxyethyl)benzene A solution of 0.5 g (1.63 mmol) of Aldehyde 1 in 10 mL of THF was treated with 1.1 mL (3.3 mmol) of methylmagnesium iodide (3.0 M in diethyl ether) at −78° C. and was allowed to warm to rt over 30 min. The resulting mixture was quenched with 5 mL of 1 N HCl and was extracted with 30 mL of ethyl acetate. The extract was washed, dried and concentrated to afford the title compound: ESI-MS 323 (M+H); LC-1: 4.2 min.

Step B: 4-(5-(4-(2-Methylpropyl)phenyl)-1,2,4-oxadiazol-3-yl)acetophenone

The title compound was prepared using a procedure analogous to that described in Aldehyde 1, Step C substituting (±)-4-(5-(4-(2-methylpropyl)phenyl)-1,2,4-oxadiazol-3-yl)-1-(1-hydroxyethyl)benzene (from Step A) for 4-(5-(4-(2-methylpropyl)phenyl)-1,2,4-oxadiazol-3-yl) phenylmethanol: ESI-MS 321 (M+H); LC-1: 4.6 min.

Step C: (±)-1-(1-(4-(5-(4-(2-Methylpropyl)phenyl)-1,2,4-oxadiazol-3-yl)phenyl)ethyl)azetidine-3-carboxylic acid The title compound was prepared using a procedure analogous to that described in Example 2 substituting 4-(5-(4-(2-methylpropyl)phenyl)-1,2,4-oxadiazol-3-yl)acetophenone for Aldehyde 12: ESI-MS 406 (M+H); LC-1: 3.5 min.

Biological Activity

The $S1P_1$/Edg1, $S1P_3$/Edg3, $S1P_2$/Edg5, $S1P_4$/Edg6 or $S1P_5$/Edg8 activity of the compounds of the present invention can be evaluated using the following assays:

Ligand Binding to Edg/S1P Receptors Assay $^{33}$P-sphingosine-1-phosphate was synthesized enzymatically from $\gamma^{33}$P-ATP and sphingosine using a crude yeast extract with sphingosine kinase activity in a reaction mix containing 50 mM $KH_2PO_4$, 1 mM mercaptoethanol, 1 mM $Na_3VO_4$, 25 mM KF, 2 mM semicarbazide, 1 mM $Na_2$EDTA, 5 mM $MgCl_2$, 50 mM sphingosine, 0.1% TritonX-114, and 1 mCi $\gamma^{33}$P-ATP (NEN; specific activity 3000 Ci/mmol). Reaction products were extracted with butanol and $^{33}$P-sphingosine-1-phosphate was purified by HPLC.

Cells expressing EDG/S1P receptors were harvested with enzyme-free dissociation solution (Specialty Media, Lavallette, N.J.). They were washed once in cold PBS and suspended in binding assay buffer consisting of 50 mM HEPES-Na, pH 7.5, 5 mM $MgCl_2$, 1 mM $CaCl_2$, and 0.5% fatty acid-free BSA. $^{33}$P-sphingosine-1-phosphate was sonicated with 0.1 nM sphingosine-1-phosphate in binding assay buffer; 100 μl of the ligand mixture was added to 100 μl cells ($1\times10^6$ cells/ml) in a 96 well microtiter dish. Binding was performed for 60 min at room temperature with gentle mixing. Cells were then collected onto GF/B filter plates with a Packard Filtermate Universal Harvester. After drying the filter plates for 30 min, 40 μl of Microscint 20 was added to each well and binding was measured on a Wallac Microbeta Scintillation Counter. Non-specific binding was defined as the amount of radioactivity remaining in the presence of 0.5 μM cold sphingosine-1-phosphate.

Alternatively, ligand binding assays were performed on membranes prepared from cells expressing Edg/S1P receptors. Cells were harvested with enzyme-free dissociation solution and washed once in cold PBS. Cells were disrupted by homogenization in ice cold 20 mM HEPES pH 7.4, 10 mM EDTA using a Kinematica polytron (setting 5, for 10 seconds). Homogenates were centrifuged at 48,000×g for 15 min at 4° C. and the pellet was suspended in 20 mM HEPES pH 7.4, 0.1 mM EDTA. Following a second centrifugation, the final pellet was suspended in 20 mM HEPES pH 7.4, 100 mM NaCl, 10 mM $MgCl_2$. Ligand binding assays were performed as described above, using 0.5 to 2 μg of membrane protein.

Agonists and antagonists of Edg/S1P receptors can be identified in the $^{33}$P-sphingosine-1-phosphate binding assay. Compounds diluted in DMSO, methanol, or other solvent, were mixed with probe containing $^{33}$P-sphingosine-1-phosphate and binding assay buffer in microtiter dishes. Membranes prepared from cells expressing Edg/S1P receptors were added, and binding to $^{33}$P-sphingosine-1-phosphate was performed as described. Determination of the amount of binding in the presence of varying concentrations of compound and analysis of the data by non-linear regression software such as MRLCalc (Merck Research Laboratories) or PRISM (GraphPad Software) was used to measure the affinity of compounds for the receptor. Selectivity of compounds for Edg/S1P receptors was determined by measuring the level of $^{33}$P-sphingosine-1-phosphate binding in the presence of the compound using membranes prepared from cells transfected with each respective receptor ($S1P_1$/Edg1, $S1P_3$/Edg3, $S1P_2$/Edg5, $S1P_4$/Edg6, $S1P_5$/Edg8).

$^{35}$S-GTPγS Binding Assay

Functional coupling of S1P/Edg receptors to G proteins was measured in a $^{35}$S-GTPγS binding assay. Membranes prepared as described in the Ligand Binding to Edg/S1P Receptors Assay (1–10 μg of membrane protein) were incubated in a 200 μl volume containing 20 mM HEPES pH 7.4, 100 mM NaCl, 10 mM $MgCl_2$, 5 μM GDP, 0.1% fatty acid-free BSA (Sigma, catalog A8806), various concentrations of sphingosine-1-phosphate, and 125 pM $^{35}$S-GTPγS (NEN; specific activity 1250 Ci/mmol) in 96 well microtiter dishes. Binding was performed for 1 hour at room temperature with gentle mixing, and terminated by harvesting the membranes onto GF/B filter plates with a Packard Filtermate Universal Harvester. After drying the filter plates for 30 min, 40 μl of Microscint 20 was added to each well and binding was measured on a Wallac Microbeta Scintillation Counter.

Agonists and antagonists of S1P/Edg receptors can be discriminated in the $^{35}$S-GTPγS binding assay. Compounds diluted in DMSO, methanol, or other solvent, were added to microtiter dishes to provide final assay concentrations of 0.01 nM to 10 μM. Membranes prepared from cells expressing S1P/Edg receptors were added, and binding to $^{35}$S-GTPγS was performed as described. When assayed in the absence of the natural ligand or other known agonist, compounds that stimulate $^{35}$S-GTPγS binding above the endogenous level were considered agonists, while compounds that inhibit the endogenous level of $^{35}$S-GTPγS binding were considered inverse agonists. Antagonists were detected in a $^{35}$S-GTPγS binding assay in the presence of a sub-maximal level of natural ligand or known S1P/Edg receptor agonist, where the compounds reduced the level of $^{35}$S-GTPγS binding. Determination of the amount of binding in the presence of varying concentrations of compound was used to measure the potency of compounds as agonists, inverse agonists, or antagonists of S1P/Edg receptors. To evaluate agonists, percent stimulation over basal was calculated as binding in the presence of compound divided by binding in the absence of ligand, multiplied by 100. Dose response curves were plotted using a non-linear regression curve fitting program MRLCalc (Merck Research Laboratories), and $EC_{50}$ values were defined to be the concentration of agonist required to give 50% of its own maximal stimulation. Selectivity of compounds for S1P/Edg receptors was determined by measuring the level of $^{35}$S-GTPγS binding in the presence of compound using membranes prepared from cells transfected with each respective receptor.

Intracellular Calcium Flux Assay

Functional coupling of S1P/Edg receptors to G protein associated intracellular calcium mobilization was measured using FLIPR (Fluorescence Imaging Plate Reader, Molecular Devices). Cells expressing S1P/Edg receptors were harvested and washed once with assay buffer (Hanks Buffered Saline Solution (BRL) containing 20 mM HEPES, 0.1% BSA and 710 μg/ml probenicid (Sigma)). Cells were labeled in the same buffer containing 500 nM of the calcium sensitive dye Fluo-4 (Molecular Probes) for 1 hour at 37° C. and 5% $CO_2$. The cells were washed twice with buffer before plating $1.5\times10^5$ per well (90 μl) in 96 well polylysine coated black microtiter dishes. A 96-well ligand plate was prepared by diluting sphingosine-1-phosphate or other agonists into 200 μl of assay buffer to give a concentration that was 2-fold the final test concentration. The ligand plate and the cell plate were loaded into the FLIPR instrument for analysis. Plates were equilibrated to 37° C. The assay was initiated by transferring an equal volume of ligand to the cell plate and the calcium flux was recorded over a 3 min interval. Cellular response was quantitated as area (sum) or maximal peak height (max). Agonists were evaluated in the absence of natural ligand by dilution of compounds into the appropriate solvent and transfer to the Fluo-4 labeled cells. Antagonists were evaluated by pretreating Fluo-4 labeled cells with varying concentrations of compounds for 15 min prior to the initiation of calcium flux by addition of the natural ligand or other S1P/Edg receptor agonist.

Preparation of Cells Expressing S1P/Edg Receptors

Any of a variety of procedures may be used to clone $S1P_1$/Edg1, $S1P_3$/Edg3, $S1P_2$/Edg5, $S1P_4$/Edg6 or $S1P_5$/Edg8. These methods include but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence; (2) direct functional expression of the Edg/S1P cDNA following the construction of an S1P/Edg-containing cDNA library in an appropriate expression vector system; (3) screening an S1P/Edg-containing cDNA library constructed in a bacteriophage or plasmid shuttle vector with a labeled degenerate oligonucleotide probe designed from the amino acid sequence of the S1P/Edg protein; (4) screening an S1P/Edg-containing cDNA library constructed in a bacteriophage or plasmid shuttle vector with a partial cDNA encoding the S1P/Edg protein. This partial cDNA is obtained by the specific PCR amplification of S1P/Edg DNA fragments through the design of degenerate oligonucleotide primers from the amino acid sequence known for other proteins which are related to the S1P/Edg protein; (5) screening an S1P/Edg-containing cDNA library constructed in a bacteriophage or plasmid shuttle vector with a partial cDNA or oligonucleotide with homology to a mammalian S1P/Edg protein. This strategy may also involve using gene-specific oligonucleotide primers for PCR amplification of S1P/Edg cDNA; or (6) designing 5' and 3' gene specific oligonucleotides using the S1P/Edg nucleotide sequence as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding S1P/Edg.

It is readily apparent to those skilled in the art that other types of libraries, as well as libraries constructed from other cell types- or species types, may be useful for isolating an S1P/Edg-encoding DNA or an S1P/Edg homologue. Other types of libraries include, but are not limited to, cDNA libraries derived from other cells.

It is readily apparent to those skilled in the art that suitable cDNA libraries may be prepared from cells or cell lines which have S1P/Edg activity. The selection of cells or cell lines for use in preparing a cDNA library to isolate a cDNA encoding S1P/Edg may be done by first measuring cell-associated S1P/Edg activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

An expression vector containing DNA encoding an S1P/Edg-like protein may be used for expression of S1P/Edg in a recombinant host cell. Such recombinant host cells can be cultured under suitable conditions to produce S1P/Edg or a biologically equivalent form. Expression vectors may include, but are not limited to, cloning vectors, modified cloning vectors, specifically designed plasmids or viruses. Commercially available mammalian expression vectors may be suitable for recombinant S1P/Edg expression.

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines.

The nucleotide sequences for the various S1P/Edg receptors are known in the art. See, for example, the following:

S1P/Edg1 Human

Hla, T. and T. Maciag 1990 An abundant transcript induced in differentiating human endothelial cells encodes a polypeptide with structural similarities to G-protein coupled receptors. J. Biol. Chem. 265:9308–9313, hereby incorporated by reference in its entirety.

WO91/15583, published on Oct. 17, 1991, hereby incorporated by reference in its entirety.

WO99/46277, published on Sep. 16, 1999, hereby incorporated by reference in its entirety.

$S1P_1$/Edg1 Mouse

WO0059529, published Oct. 12, 2000, hereby incorporated by reference in its entirety.

U.S. Pat. No. 6,323,333, granted Nov. 27, 2001, hereby incorporated by reference in its entirety.

$S1P_1$/Edg1 Rat

Lado, D. C., C. S. Browe, A. A. Gaskin, J. M. Borden, and A. J. MacLennan. 1994 Cloning of the rat edg-1 immediate-early gene: expression pattern suggests diverse functions. Gene 149: 331–336, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

$S1P_3$/Edg3 Human

An, S., T. Bleu, W. Huang, O. G. Hallmark, S. R. Coughlin, E. J. Goetzl 1997 Identification of cDNAs encoding two G protein-coupled receptors for lysosphingolipids FEBS Lett. 417:279–282, hereby incorporated by reference in its entirety.

WO 99/60019, published Nov. 25, 1999, hereby incorporated by reference in its entirety.

U.S. Pat. No. 6,130,067, granted Oct. 10, 2000, hereby incorporated by reference in its entirety.

$S1P_3$/Edg3 Mouse

WO 01/11022, published Feb. 15, 2001, hereby incorporated by reference in its entirety.

$S1P_3$/Edg3 Rat

WO 01/27137, published Apr. 19, 2001, hereby incorporated by reference in its entirety.

$S1P_2$/Edg5 Human

An, S., Y. Zheng, T. Bleu 2000 Sphingosine 1-Phosphate-induced cell proliferation, survival, and related signaling events mediated by G Protein-coupled receptors Edg3 and Edg5. J. Biol. Chem 275: 288–296, hereby incorporated by reference in its entirety.

WO 99/35259, published Jul. 15, 1999, hereby incorporated by reference in its entirety.

WO99/54351, published Oct. 28, 1999, hereby incorporated by reference in its entirety.

WO 00/56135, published Sep. 28, 2000, hereby incorporated by reference in its entirety.

$S1P_2$/Edg5 Mouse

WO 00/60056, published Oct. 12, 2000, hereby incorporated by reference in its entirety.

$S1P_2$/Edg5 Rat

Okazaki, H., N. Ishizaka, T. Sakurai, K. Kurokawa, K. Goto, M. Kumada, Y. Takuwa 1993 Molecular cloning of a novel putative G protein-coupled receptor expressed in the cardiovascular system. Biochem. Biophys. Res. Comm. 190:1104–1109, hereby incorporated by reference in its entirety.

MacLennan, A. J., C. S. Browe, A. A. Gaskin, D. C. Lado, G. Shaw 1994 Cloning and characterization of a putative G-protein coupled receptor potentially involved in development. Mol. Cell. Neurosci. 5: 201–209, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

$S1P_4$/Edg6 Human

Graler, M. H., G. Bernhardt, M. Lipp 1998 EDG6, a novel G-protein-coupled receptor related to receptors for bioactive lysophospholipids, is specifically expressed in lymphoid tissue. Genomics 53: 164–169, hereby incorporated by reference in its entirety.

WO 98/48016, published Oct. 29, 1998, hereby incorporated by reference in its entirety.

U.S. Pat. No. 5,912,144, granted Jun. 15, 1999, hereby incorporated by reference in its entirety.

WO 98/50549, published Nov. 12, 1998, hereby incorporated by reference in its entirety.

U.S. Pat. No. 6,060,272, granted May 9, 2000, hereby incorporated by reference in its entirety.

WO 99/35106, published Jul. 15, 1999, hereby incorporated by reference in its entirety.

WO 00/15784, published Mar. 23, 2000, hereby incorporated by reference in its entirety.

WO 00/14233, published Mar. 16, 2000, hereby incorporated by reference in its entirety.

$S1P_4$/Edg6 Mouse

WO 00/15784, published Mar. 23, 2000, hereby incorporated by reference in its entirety.

$S1P_5$/Edg8 Human

Im, D.-S., J. Clemens, T. L. Macdonald, K. R. Lynch 2001 Characterization of the human and mouse sphingosine 1-phosphate receptor, $S1P_5$ (Edg-8): Structure-Activity relationship of sphingosine 1-phosphate receptors. Biochemistry 40:14053–14060, hereby incorporated by reference in its entirety.

WO 00/11166, published Mar. 2, 2000, hereby incorporated by reference in its entirety.

WO 00/31258, published Jun. 2, 2000, hereby incorporated by reference in its entirety.

WO 01/04139, published Jan. 18, 2001, hereby incorporated by reference in its entirety.

EP 1 090 925, published Apr. 11, 2001, hereby incorporated by reference in its entirety.

$S1P_5$/Edg8 Rat

Im, D.-S., C. E. Heise, N. Ancellin, B. P. O'Dowd, G.-J. Shei, R. P. Heavens, M. R. Rigby, T. Hla, S. Mandala, G. McAllister, S. R. George, K. R. Lynch 2000 Characterization of a novel sphingosine 1-phosphate receptor, Edg-8. J. Biol. Chem. 275: 14281–14286, hereby incorporated by reference in its entirety.

WO 01/05829, published Jan. 25, 2001, hereby incorporated by reference in its entirety.

Measurement of Cardiovascular Effects

The effects of compounds of the present invention on cardiovascular parameters can be evaluated by the following procedure:

Adult male rats (approx. 350 g body weight) were instrumented with femoral arterial and venous catheters for measurement of arterial pressure and intravenous compound administration, respectively. Animals were anesthetized with Nembutal (55 mg/kg, ip). Blood pressure and heart rate were recorded on the Gould Po-Ne-Mah data acquisition system. Heart rate was derived from the arterial pulse wave. Following an acclimation period, a baseline reading was taken (approximately 20 minutes) and the data averaged. Compound was administered intravenously (either bolus injection of approximately 5 seconds or infusion of 15 minutes duration), and data were recorded every 1 minute for 60 minutes post compound administration. Data are calculated as either the peak change in heart rate or mean arterial pressure or are calculated as the area under the curve for changes in heart rate or blood pressure versus time. Data are expressed as mean±SEM. A one-tailed Student's paired t-test is used for statistical comparison to baseline values and considered significant at $p<0.05$.

The S1P effects on the rat cardiovascular system are described in Sugiyama, A., N. N. Aye, Y. Yatomi, Y. Ozaki, K. Hashimoto 2000 Effects of Sphingosine-1-Phosphate, a naturally occurring biologically active lysophospholipid, on the rat cardiovascular system. Jpn. J. Pharmacol. 82: 338–342, hereby incorporated by reference in its entirety.

Measurement of Mouse Acute Toxicity

A single mouse is dosed intravenously (tail vein) with 0.1 ml of test compound dissolved in a non-toxic vehicle and is observed for signs of toxicity. Severe signs may include death, seizure, paralysis or unconciousness. Milder signs are also noted and may include ataxia, labored breathing, ruffling or reduced activity relative to normal. Upon noting signs, the dosing solution is diluted in the same vehicle. The diluted dose is administered in the same fashion to a second mouse and is likewise observed for signs. The process is repeated until a dose is reached that produces no signs. This is considered the estimated no-effect level. An additional mouse is dosed at this level to confirm the absence of signs.

Assessment of Lymphopenia

Compounds are administered as described in Measurement of Mouse Acute Toxicity and lymphopenia is assessed in mice at three hours post dose as follows. After rendering a mouse unconscious by $CO_2$ to effect, the chest is opened, 0.5 ml of blood is withdrawn via direct cardiac puncture, blood is immediately stabilized with EDTA and hematology is evaluated using a clinical hematology autoanalyzer calibrated for performing murine differential counts (H2000, CARESIDE, Culver City Calif.). Reduction in lymphocytes by test treatment is established by comparison of hematological parameters of three mice versus three vehicle treated mice. The dose used for this evaluation is determined by tolerability using a modification of the dilution method above. For this purpose, no-effect is desirable, mild effects are acceptable and severely toxic doses are serially diluted to levels that produce only mild effects.

In Vitro Activity of Examples

The examples disclosed herein have utility as immunoregulatory agents as demonstrated by their activity as potent and selective agonists of the $S1P_1$/Edg1 receptor over the $S1PR_3$/Edg3 receptor as measured in the assays described above. In particular, the examples disclosed herein possess a selectivity for the $S1P_1$/Edg1 receptor over the $S1PR_3$/Edg3 receptor of more than 500 fold as measured by the ratio of $EC_{50}$ for the $S1P_1$/Edg1 receptor to the $EC_{50}$ for the $S1P_3$/Edg3 receptor as evaluated in the $^{35}$S-GTPγS binding assay described above and possess an $EC_{50}$ for binding to the $S1P_1$/Edg1 receptor of less than 50 nM as evaluated by the $^{35}$S-GTPγS binding assay described above.

What is claimed is:

1. A compound represented by Formula I:

I

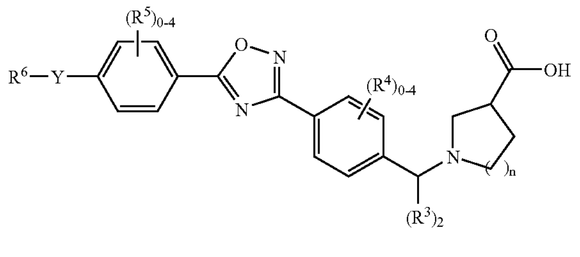

or a pharmaceutically acceptable salt or hydrate thereof, wherein:

n is 0;

Y is a bond, —O— or —S(O)$_k$—, wherein k is 0, 1 or 2;

each $R^3$ is independently selected from the group consisting of: hydrogen and $C_{1-4}$alkyl, said $C_{1-4}$alkyl optionally substituted with from one up to the maximum number of substitutable positions with a substituent independently selected from the group consisting of: halo, hydroxy, $C_{1-4}$alkoxy and carboxy;

each $R^4$ is independently selected from the group consisting of: halo, hydroxy, $C_{1-4}$alkyl and $C_{1-3}$alkoxy, said $C_{1-4}$ alkyl and $C_{1-3}$alkoxy groups optionally substituted from one up to the maximum number of substitutable positions with halo;

each $R^5$ is independently selected from the group consisting of:

(a) halo,
(b) cyano,
(c) hydroxy,
(d) —N($R^7$)$_2$
(e) $C_{1-6}$alkyl,
(f) $C_{2-6}$alkenyl,
(g) $C_{3-6}$alkynyl
(h) $C_{1-6}$alkoxy
(i) $C_{1-6}$alkyl-S(O)$_k$—, wherein k is 0, 1 or 2,
(j) $C_{3-6}$cycloalkyl,
(k) phenyl, and
(l) $HET^1$;

wherein items (e) to (j) above are each optionally substituted from one up to the maximum number of substituable positions with a substituent independently selected from the group consisting of: halo, hydroxy and $C_{1-3}$alkoxy, said $C_{1-3}$alkoxy group optionally substituted from one up to the maximum number of substitutable positions with halo, and wherein items (k) and (l) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo;

$R^6$ is selected from the group consisting of:

(1) hydrogen
(2) halo,
(3) cyano,
(4) $C_{1-10}$alkyl,
(5) $C_{2-10}$alkenyl,
(6) $C_{3-10}$alkynyl,
(7) $C_{3-6}$cycloalkyl
(8) phenyl, and
(9) $HET^2$;

wherein items (4) to (6) above are each optionally substituted from one up to the maximum number of substituable positions with a substituent independently selected from the group consisting of: halo, hydroxy, $C_{3-6}$cycloalkyl, phenyl, $HET^3$ and $C_{1-3}$alkoxy, said $C_{3-6}$cycloalkyl, phenyl, $HET^3$ and $C_{1-3}$alkoxy groups optionally substituted from one up to the maximum number of substitutable positions with halo, wherein item (7) above is optionally substituted from one up to the maximum number of substituable positions with a substituent independently selected from the group consisting of: halo, hydroxy, phenyl, $HET^4$ and $C_{1-3}$alkoxy, said phenyl, $HET^4$ and $C_{1-3}$alkoxy groups optionally substituted from one up to the maximum number of substitutable positions with halo, and wherein items (8) and (9) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo, with the provsio that $R^6$ is not halo or cyano when Y is —O— or —S(O)$_k$—; or $R^6$ and one $R^5$ group or two $R^5$ groups may be joined together to form a five or six-membered monocyclic ring optionally containing 1 or 2 heteroatoms selected from the group consisting of: O, S, or N($R^7$), each $R^7$ is independently hydrogen or $C_{1-4}$alkyl, said $C_{1-4}$alkyl optionally substituted substituted from one up to the maximum number of substitutable positions with halo; and $HET^1$, $HET^2$, $HET^3$ and $HET^4$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

2. The compound according to claim 1 wherein $R^3$ is hydrogen or methyl.

3. The compound according to claim 1 wherein one $R^4$ is present and said $R^4$ is halo or methyl.

4. The compound according to claim 1 wherein no $R^5$ is present.

5. The compound according to claim 1 wherein $R^6$ is selected from the group consisting of:

(1) $C_{1-10}$alkyl, (2) $C_{2-10}$alkenyl, (3) $C_{3-10}$alkynyl, (4) $C_{3-6}$cycloalkyl (5) phenyl, and (6) $HET^2$;

wherein items (1) to (3) above are each optionally substituted from one up to the maximum number of substituable positions with a substituent independently selected from the group consisting of: halo, hydroxy, $C_{3-6}$cycloalkyl, phenyl, $HET^3$ and $C_{1-3}$alkoxy, said $C_{3-6}$cycloalkyl, phenyl, $HET^3$ and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl, $HET^4$ and $C_{1-3}$alkoxy, said phenyl, $HET^4$ and $C_{1-3}$alkoxy groups optionally substituted from one up to the maximum number of substitutable positions with halo, and wherein items (5) and (6) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo.

6. The compound according to claim 5 wherein $R^6$ is selected from the group consisting of:

(1) $C_{1-10}$alkyl, (2) $C_{2-10}$alkenyl, (3) $C_{3-10}$alkynyl, (4) $C_{3-6}$cycloalkyl and (5) phenyl, wherein items (1) to (3) above are each optionally substituted from one up to the maximum number of substituable positions with a substituent independently selected from the group consisting of: halo, hydroxy, $C_{3-6}$cycloalkyl, phenyl and $C_{1-3}$alkoxy, said $C_{3-6}$cycloalkyl, phenyl and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl and $C_{1-3}$alkoxy, said phenyl and $C_{1-3}$alkoxy groups optionally substituted from one up to the maximum number of substitutable positions with halo, and wherein item (5) above is optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo.

7. The compound according to claim 1 of Formula Ia:

Ia

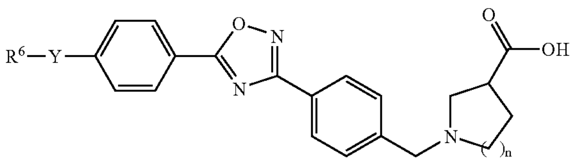

or a pharmaceutically acceptable salt or hydrate thereof, wherein:

n is 0;

Y is a bond or —O—;

$R^6$ is selected from the group consisting of:

(1) $C_{1-10}$alkyl, (2) $C_{2-10}$alkenyl, (3) $C_{3-10}$alkynyl, (4) $C_{3-6}$cycloalkyl (5) phenyl, and (6) $HET^2$;

wherein items (1) to (3) above are each optionally substituted from one up to the maximum number of substituable positions with a substituent independently selected from the group consisting of: halo, hydroxy, $C_{3-6}$cycloalkyl, phenyl, $HET^3$ and $C_{1-3}$alkoxy, said $C_{3-6}$cycloalkyl, phenyl, $HET^3$ and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl, $HET^4$ and $C_{1-3}$alkoxy, said phenyl, $HET^4$ and $C_{1-3}$alkoxy groups optionally substituted from one up to the maximum number of substitutable positions with halo, and wherein items (5) and (6) above are each optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo; and $HET^2$, $HET^3$ and $HET^4$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

8. The compound according to claim 7 wherein $R^6$ is selected from the group consisting of:

(1) $C_{1-10}$alkyl, (2) $C_{2-10}$alkenyl, (3) $C_{3-10}$alkynyl, (4) $C_{3-6}$cycloalkyl and (5) phenyl, wherein items (1) to (3) above are each optionally substituted from one up to the maximum number of substituable positions with a substituent independently selected from the group consisting of: halo, hydroxy, $C_{3-6}$cycloalkyl, phenyl and $C_{1-3}$alkoxy, said $C_{3-6}$cycloalkyl, phenyl and $C_{1-3}$alkoxy groups optionally substituted from one up to the maximum number of substitutable positions with halo, wherein item (4) above is optionally substituted from one up to the maximum number of substituable positions with a substituent independently selected from the group consisting of: halo, hydroxy, phenyl and $C_{1-3}$alkoxy, said phenyl and $C_{1-3}$alkoxy groups optionally substituted from one up to the maximum number of substitutable positions with halo, and wherein item (5) above is optionally substituted from one up to the maximum number of substituable positions with a substituent independently selected from the group consisting of: halo, hydroxy, $C_{1-4}$alkyl and $C_{1-3}$alkoxy, said $C_{1-4}$alkyl and $C_{1-3}$alkoxy groups optionally substituted from one up to the maximum number of substitutable positions with halo.

9. The compound according to claim 7 wherein Y is a bond and $R^6$ is $C_{1-6}$alkyl.

10. A compound selected from the following table:

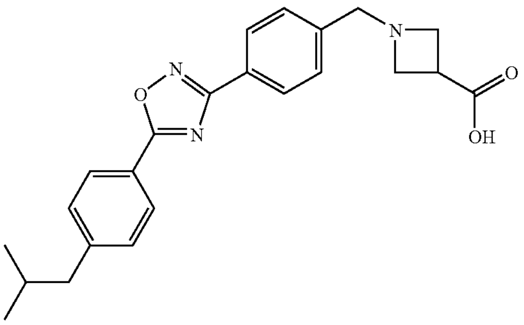

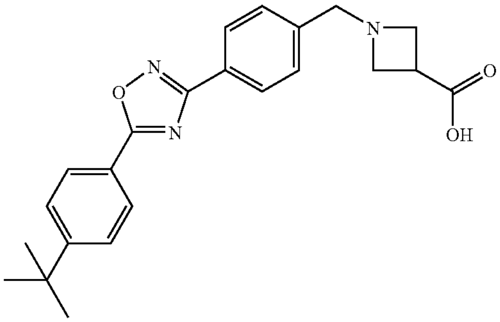

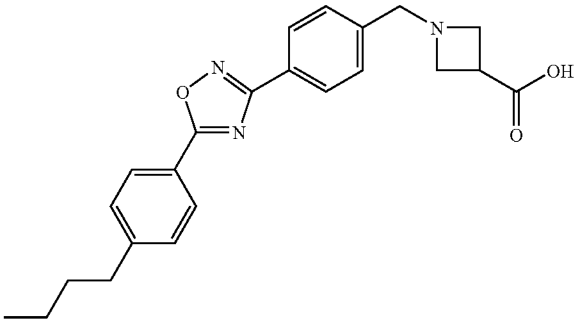

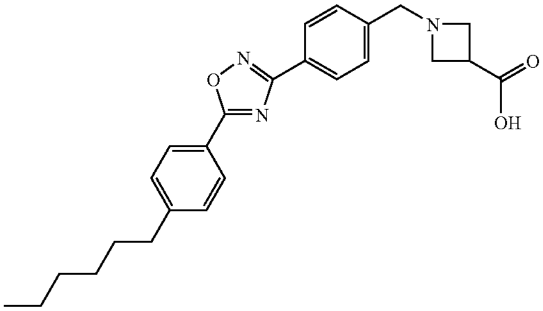

-continued
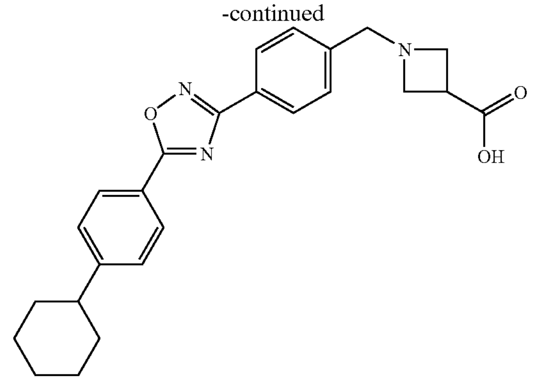
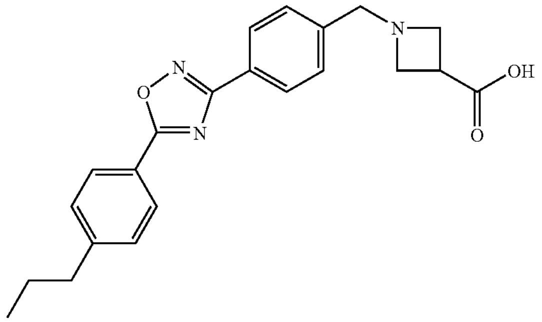
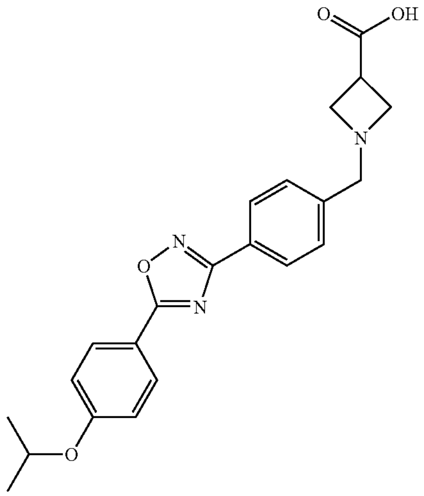
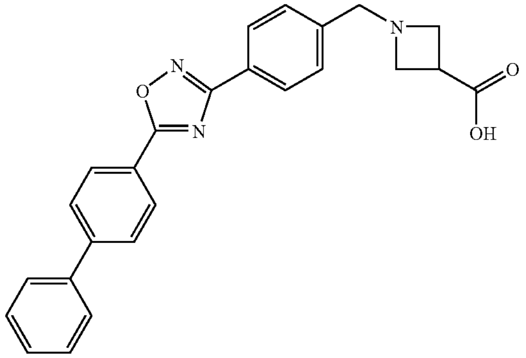
-continued
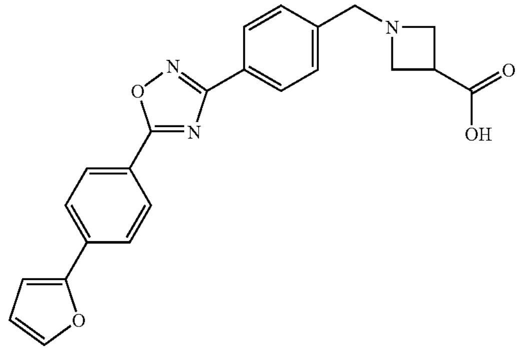
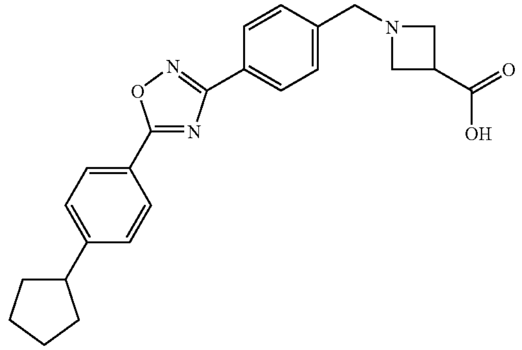
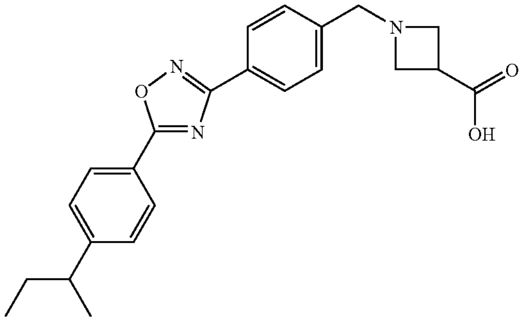
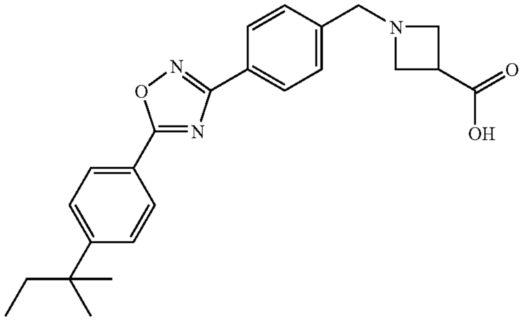
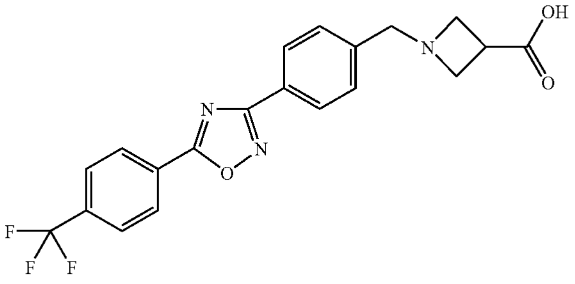

-continued

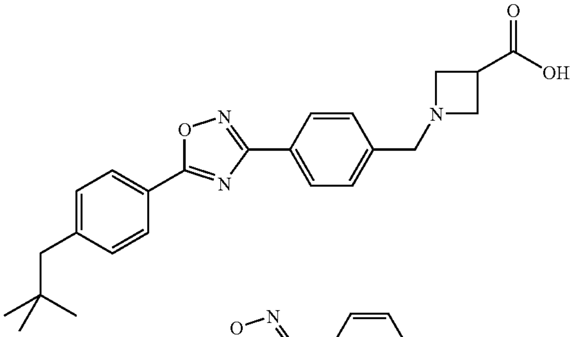

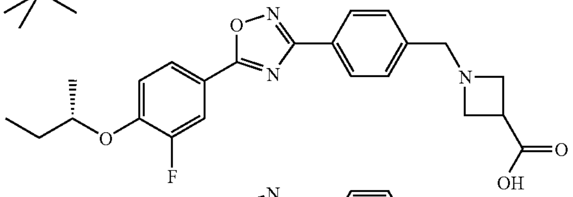

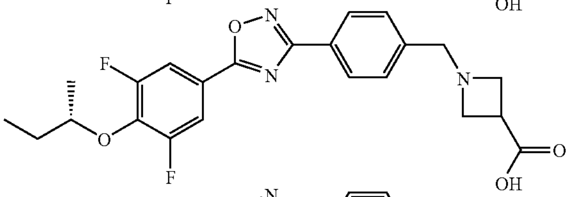

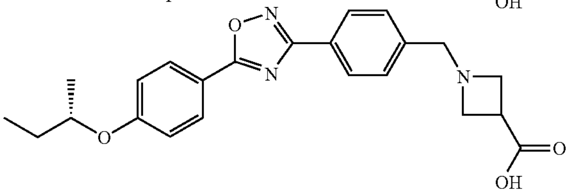

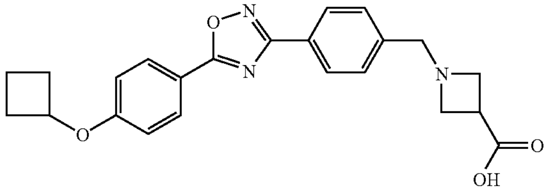

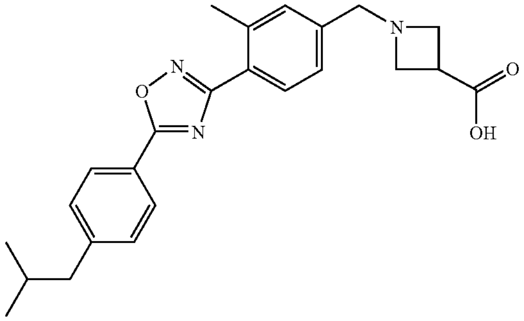

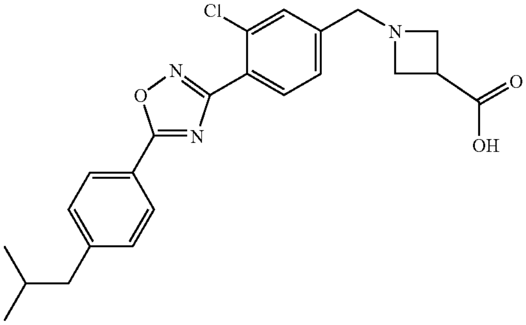

-continued

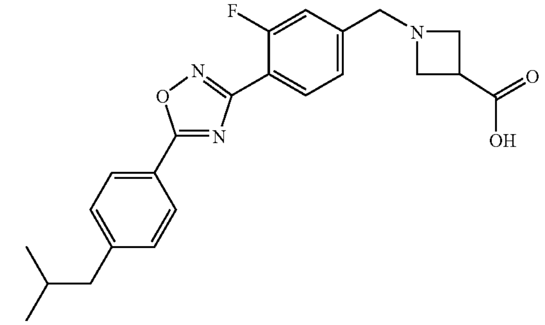

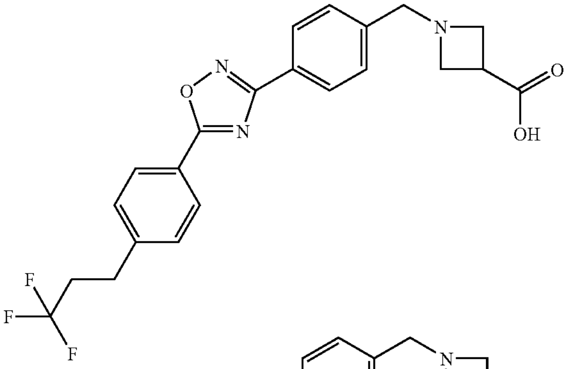

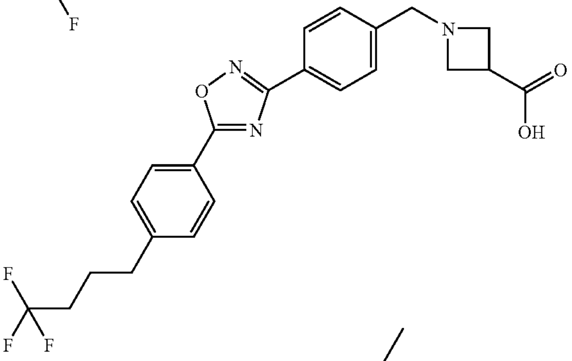

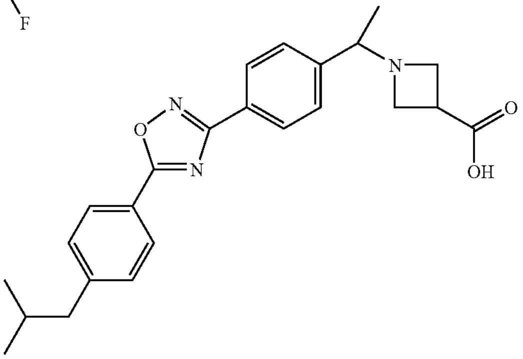

or a pharmaceutically acceptable salt or hydrate thereof.

11. A method of treating an immunoregulatory abnormality in a mammalian patient in need of such treatment comprising administering to said patient a compound in accordance with claim 1 in an amount that is effective for treating said immunoregulatory abnormality, wherein the immunoregulatory abnormality is bone marrow or oman transplant rejection.

12. A pharmaceutical composition comprised of a compound in accordance with claim 1 in combination with a pharmaceutically acceptable carrier.

* * * * *